(12) United States Patent  
Inoue et al.

(10) Patent No.: US 9,444,059 B2  
(45) Date of Patent: Sep. 13, 2016

(54) ORGANOMETALLIC COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Yui Yamada, Kanagawa (JP); Hiromi Seo, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 179 days.

(21) Appl. No.: 14/184,130

(22) Filed: Feb. 19, 2014

(65) Prior Publication Data

US 2014/0231770 A1 Aug. 21, 2014

(30) Foreign Application Priority Data

Feb. 21, 2013 (JP) ................................ 2013-031622

(51) Int. Cl.
| | |
|---|---|
| *H01L 51/54* | (2006.01) |
| *C09K 11/06* | (2006.01) |
| *H01L 51/00* | (2006.01) |
| *C07F 15/00* | (2006.01) |
| *H01L 51/50* | (2006.01) |

(52) U.S. Cl.
CPC ....... *H01L 51/0085* (2013.01); *C07F 15/0033* (2013.01); *C09K 11/06* (2013.01);
(Continued)

(58) Field of Classification Search
None
See application file for complete search history.

(56) References Cited

U.S. PATENT DOCUMENTS 7,649,077 B2  1/2010  Craig et al.
8,012,602 B2  9/2011  Schafer et al.
(Continued)

FOREIGN PATENT DOCUMENTS

JP  2011-181660 A  * 9/2011
KR  2012-0117693     10/2012
(Continued)

OTHER PUBLICATIONS

Machine translation of JP 2011-181660 A (Sep. 2011).*
(Continued)

*Primary Examiner* — Marie R. Yamnitzky
(74) *Attorney, Agent, or Firm* — Husch Blackwell LLP

(57) ABSTRACT

A novel substance capable of emitting phosphorescence is provided. An organometallic complex represented by General Fomulae (G3) or (G5). In the formulae, M represents iridium, platinum, palladium, or rhodium, $R^1$ represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms.

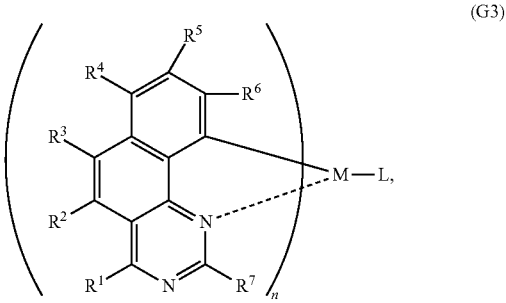

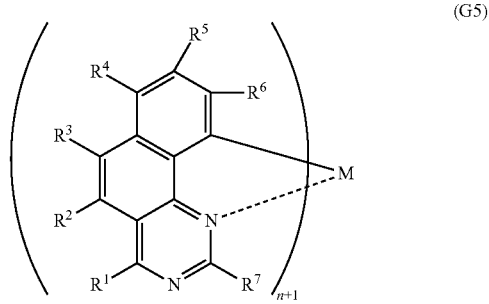

20 Claims, 20 Drawing Sheets

(52) U.S. Cl.
CPC ....... *H01L51/0084* (2013.01); *H01L 51/0087* (2013.01); *C09K 2211/1007* (2013.01); *C09K 2211/1044* (2013.01); *C09K 2211/185* (2013.01); *H01L 51/006* (2013.01); *H01L 51/0059* (2013.01); *H01L 51/0072* (2013.01); *H01L 51/0074* (2013.01); *H01L 51/5016* (2013.01)

(56) References Cited

U.S. PATENT DOCUMENTS

| | | | |
|---|---|---|---|
| 2007/0122655 A1* | 5/2007 | Deaton et al. | C09K 11/06 428/690 |
| 2010/0240892 A1 | 9/2010 | Schafer et al. | |
| 2013/0079517 A1 | 3/2013 | Schafer et al. | |

FOREIGN PATENT DOCUMENTS

| | | |
|---|---|---|
| WO | WO 0070655 | 11/2000 |
| WO | WO 2013180376 | 12/2013 |

OTHER PUBLICATIONS

Herrera, A. et al, "The Reaction of Tetralones with Nitriles: A Simple Approach to the Synthesis of New Substituted benzo[h]quinazolines, benzo[f]quinazolines and dibenzo[a,i]phenanthridines," Tetrahedron, 2006, vol. 62, Issue 12, pp. 2799-2811.

* cited by examiner

FIG. 4A
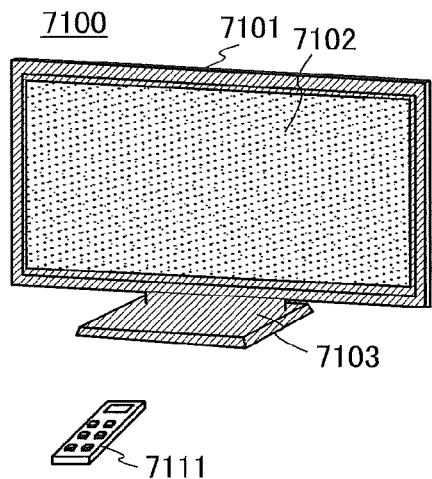
FIG. 4B
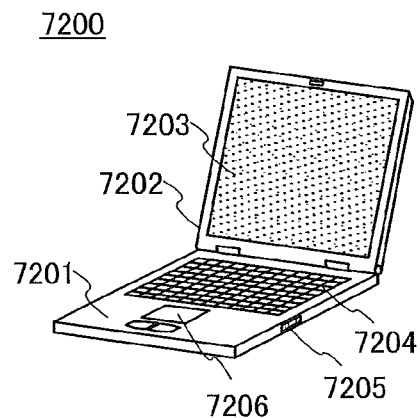
FIG. 4C
FIG. 4D
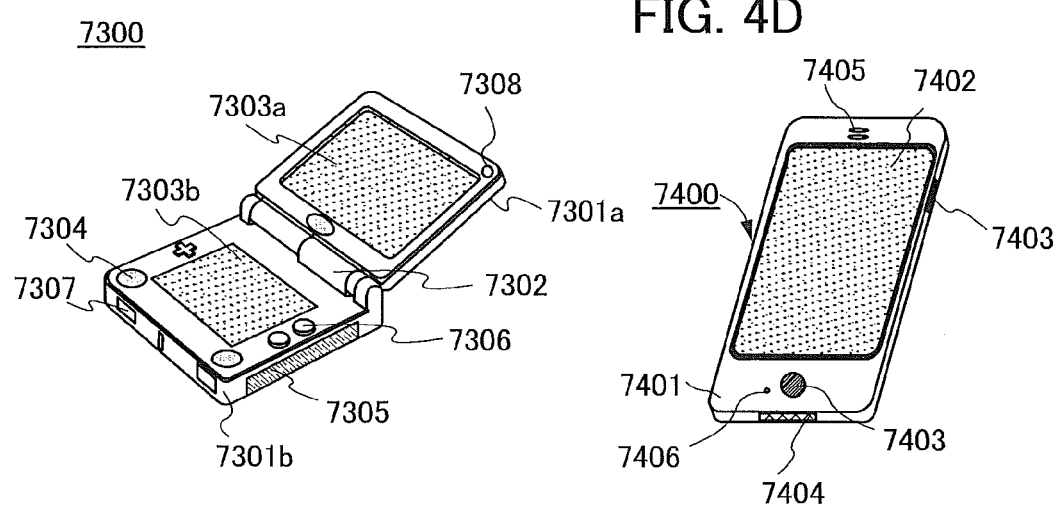
FIG. 4E
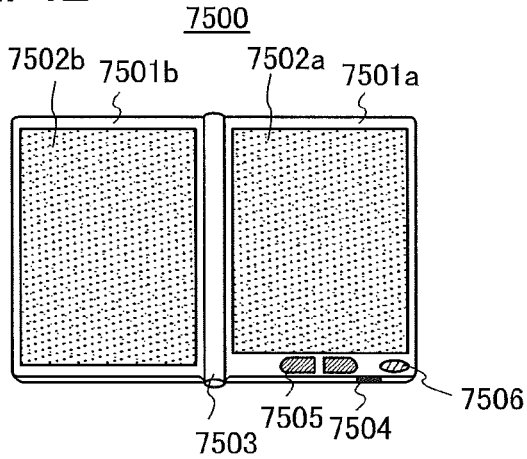

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

One embodiment of the present invention relates to a semiconductor device, a display device, a light-emitting device, a driving method thereof, or a fabrication method thereof. One embodiment of the present invention relates to an organometallic complex. In particular, one embodiment of the present invention relates to an organometallic complex that is capable of converting a triplet excited state into luminescence. In addition, one embodiment of the present invention relates to a light-emitting element, a light-emitting device, an electronic device, and a lighting device each using the organometallic complex.

2. Description of the Related Art

In recent years, a light-emitting element using a light-emitting organic compound or inorganic compound as a light-emitting substance has been actively developed. In particular, a light-emitting element called an electroluminescence (EL) element has attracted attention as a next-generation flat panel display element because it has a simple structure in which a light-emitting layer containing a light-emitting substance is provided between electrodes, and characteristics such as feasibility of being thin, lightweight, and highly responsive to input signals, and able to be driven with direct current at low voltage. In addition, a display using such a light-emitting element has a feature that it is excellent in contrast and image quality, and has a wide viewing angle. Further, since such a light-emitting element is a plane light source, the light-emitting element is considered applicable to a light source such as a backlight of a liquid crystal display and lighting.

In the case where the light-emitting substance is an organic compound having a light-emitting property, the emission mechanism of the light-emitting element is of a carrier-injection type. That is, by applying voltage with a light-emitting layer provided between electrodes, electrons and holes injected from the electrodes recombine to put the light-emitting substance into an excited state, and light is emitted when the excited state returns to a ground state. There are two types of the excited states that are possible: a singlet excited state (S*) and a triplet excited state (T*). In addition, the statistical generation ratio of S* to T* in a light-emitting element is thought to be 1:3.

In general, the ground state of a light-emitting organic compound is a singlet state. Light emission from the singlet excited state (S*) is referred to as fluorescence where electron transition occurs between the same multiplicities. On the other hand, light emission from the triplet excited state (T*) is referred to as phosphorescence where electron transition occurs between different multiplicities. At room temperature, observations of a compound which emits fluorescence (hereinafter referred to as a fluorescent compound) usually show only fluorescence without phosphorescence. Therefore, the internal quantum efficiency (the ratio of the number of generated photons to the number of injected carriers) of a light-emitting element including the fluorescent compound is assumed to have a theoretical limit of 25%, on the basis of S*:T*=1:3.

On the other hand, when a phosphorescent compound is used as a light-emitting organic compound, the internal quantum efficiency can be theoretically increased to 100%. In other words, the emission efficiency can be four times as much as that of the fluorescent compound. For this reason, light-emitting elements using phosphorescent compounds have been recently under active development so that high-efficiency light-emitting elements can be achieved. As the phosphorescent compound, an organometallic complex that has iridium or the like as a central metal has particularly attracted attention because of its high phosphorescence quantum yield; for example, an organometallic complex that has iridium as a central metal is disclosed as a phosphorescent material in Patent Document 1.

An advantage of use of the highly-efficient light-emitting element is that power consumption of an electronic device using the light-emitting element can be reduced, for example. With recent attention to the energy problems, power consumption is becoming a major factor affecting the trends in consumer purchases and thus attains considerable importance.

REFERENCE

Patent Document

[Patent Document 1] International Publication WO 00/70655 pamphlet

SUMMARY OF THE INVENTION

An object of one embodiment of the present invention is to provide a novel substance that can emit phosphorescence. Another object is to provide a light-emitting element, a light-emitting device, an electronic device, or a lighting device using the novel substance.

Another object of one embodiment of the present invention is to provide a light-emitting element with high emission efficiency. Another object of one embodiment of the present invention is to provide a light-emitting device with high emission efficiency. Another object of one embodiment of the present invention is to provide an electronic device or a lighting device with low power consumption. Another object of one embodiment of the present invention is to provide a light-emitting element or the like with a long lifetime. Another object of one embodiment of the present invention is to provide a light-emitting element or the like with high reliability.

Note that the descriptions of these objects do not disturb the existence of other objects. All the objects are not necessarily needed to be achieved simultaneously in one embodiment of the present invention. Other objects may be apparent from the description of the specification, the drawings, the claims, and the like.

An organometallic complex of one embodiment of the present invention contains at least any one of metals of iridium, platinum, palladium, and rhodium and a ligand with a benzoquinazoline skeleton. Specifically, one embodiment of the present invention is an organometallic complex having a structure represented by General Formula (G1).

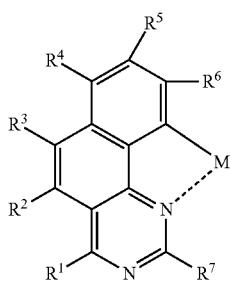

(G1)

In General Formula (G1), M represents iridium, platinum, palladium, or rhodium, $R^1$ represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms.

In General Formula (G1), $R^2$ to $R^7$ are preferably hydrogen, in which case the synthesis is facilitated.

One embodiment of the present invention is an organometallic complex represented by General Formula (G3).

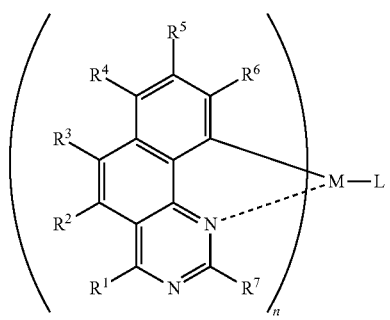

(G3)

In General Formula (G3), M represents iridium, platinum, palladium, or rhodium, $R^1$ represents a substituted or unsubstituted alkyl group having 1 to 6 carbon atoms, or a substituted or unsubstituted aryl group having 6 to 10 carbon atoms, $R^2$ to $R^7$ separately represent hydrogen or a substituted or unsubstituted alkyl group having 1 to 6 carbon atoms, and L represents a monoanionic ligand. When M represents iridium or rhodium, n is 2. When M represents platinum or palladium, n is 1.

In General Formula (G3), $R^2$ to $R^7$ are preferably hydrogen, in which case the synthesis is facilitated.

In the organometallic complex of one embodiment of the present invention represented by General Formula (G3), the monoanionic ligand is preferably a monoanionic bidentate chelate ligand with a beta-diketone structure or a monoanionic bidentate chelate ligand in which two coordinating elements are both nitrogen. The monoanionic ligand is preferably represented by General Formula (L1) or (L2).

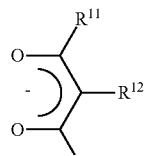

(L1)

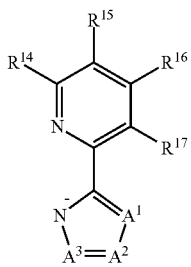

(L2)

$R^{11}$ to $R^{17}$ in General Formulae (L1) and (L2) separately represent hydrogen or a substituted or unsubstituted alkyl group having 1 to 6 carbon atoms, $A^1$ to $A^3$ separately represent nitrogen or carbon bonded to hydrogen or a substituent R. The substituent R represents an alkyl group having 1 to 6 carbon atoms or a phenyl group.

One embodiment of the present invention is an organometallic complex represented by General Formula (G5).

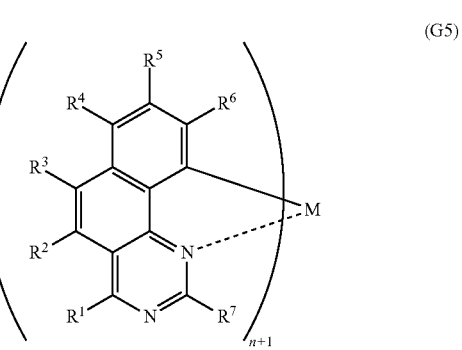

(G5)

In General Formula (G5), M represents iridium, platinum, palladium, or rhodium $R^1$ represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms. When M represents iridium or rhodium, n is 2. When M represents platinum or palladium, n is 1.

In General Formula (G5), $R^2$ to $R^7$ are preferably hydrogen, in which case the synthesis is facilitated.

One embodiment of the present invention is a light-emitting element including, between a pair of electrodes, any of the organometallic complexes described above. Specifically, it is preferable that the light-emitting element include, between the pair of electrodes, a light-emitting layer containing any of the organometallic complexes described above.

One embodiment of the present invention is a light-emitting device including the above-described light-emitting element. One embodiment of the present invention is a display device including the light-emitting device in a display portion. One embodiment of the present invention is a lighting device including the light-emitting device in a lighting portion.

The light-emitting device in this specification includes an image display device that uses a light-emitting element. The category of the light-emitting device in this specification may include a module in which a light-emitting element is provided with a connector such as an anisotropic conductive film or a tape carrier package (TCP); a module in which a printed wiring board is provided at the end of a TCP; a module in which an integrated circuit (IC) is directly mounted on a light-emitting element by a chip on glass (COG) method; and a module provided with a touch sensor. That is, the module can be regarded as the light-emitting device described in this specification.

According to one embodiment of the present invention, a novel substance capable of emitting phosphorescence can be provided. According to one embodiment of the present invention, a light-emitting element, a light-emitting device, an electronic device, or a lighting device using the novel substance can be provided.

BRIEF DESCRIPTION OF THE DRAWINGS

FIGS. 4A to 4E illustrate examples of an electronic device.

DETAILED DESCRIPTION OF THE INVENTION

Figure 1A:
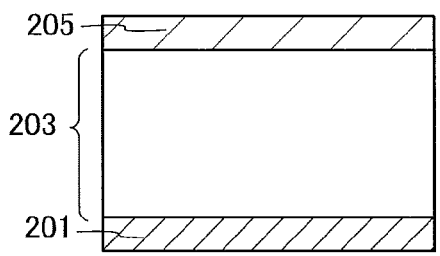
FIGS. 1A to 1D illustrate examples of a light-emitting element.

Embodiments of the present invention will be described with reference to the drawings. Note that the present invention is not limited to the following description, and it is easily understood by those skilled in the art that various changes for embodiments and details can be made without departing from the spirit and scope of the invention. Therefore, the present invention should not be construed as being limited to the description in the following embodiments. Note that in the structures of the invention described below, the same portions or portions having similar functions are denoted by the same reference numerals in different drawings, and description of such portions is not repeated.

Embodiment 1

In this embodiment, the organometallic complex of one embodiment of the present invention will be described.

The organometallic complex of one embodiment of the present invention contains at least any one of metals of iridium, platinum, palladium, and rhodium and a ligand with a benzoquinazoline skeleton.

Specifically, one embodiment of the present invention is an organometallic complex having a structure represented by General Formula (G1).

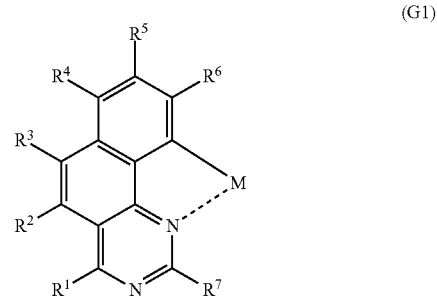

(G1)

In General Formula (G1), M represents iridium, platinum, palladium, or rhodium, le represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms.

Specific examples of the alkyl group having 1 to 6 carbon atoms include a methyl group, an ethyl group, an n-propyl group, an isopropyl group, an n-butyl group, a sec-butyl group, an isobutyl group, a tert-butyl group, an n-hexyl group, an n-pentyl group, an isopentyl group, a sec-pentyl group, a tert-pentyl group, a neopentyl group, a hexyl group, an isohexyl group, a sec-hexyl group, a tert-hexyl group, a neohexyl group, a 3-methylpentyl group, a 2-methylpentyl group, a 2-ethylbutyl group, a 1,2-dimethylbutyl group, and a 2,3-dimethylbutyl group.

As the aryl group having 6 to 10 carbon atoms, an unsubstituted phenyl group, a phenyl group substituted by one or more alkyl groups each having 1 to 4 carbon atoms, a phenyl group substituted by one or more alkoxy groups each having 1 to 4 carbon atoms, a phenyl group substituted by one or more alkylthio groups each having 1 to 4 carbon atoms, a phenyl group substituted by one or more aryl groups each having 6 to 10 carbon atoms, a phenyl group substituted by one or more halogens, a phenyl group substituted by one or more haloalkyl groups each having 1 to 4 carbon atoms, a substituted or unsubstituted naphthalene-yl group, and the like can be given.

One embodiment of the present invention is an organometallic complex having a structure represented by General Formula (G2).

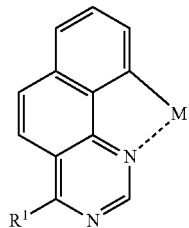

(G2)

In General Formula (G2), M represents iridium, platinum, palladium, or rhodium, and $R^1$ represents a substituted or unsubstituted alkyl group having 1 to 6 carbon atoms, or a substituted or unsubstituted aryl group having 6 to 10 carbon atoms.

One embodiment of the present invention is an organometallic complex represented by General Formula (G3).

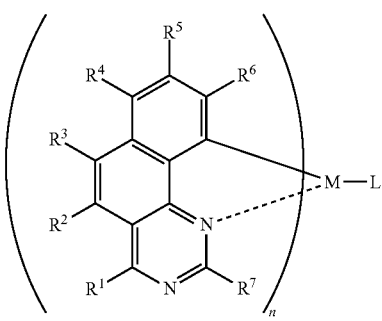

(G3)

In General Formula (G3), M represents iridium, platinum, palladium, or rhodium, $R^1$ represents a substituted or unsubstituted alkyl group having 1 to 6 carbon atoms, or a substituted or unsubstituted aryl group having 6 to 10 carbon atoms, $R^2$ to $R^7$ separately represent hydrogen or a substituted or unsubstituted alkyl group having 1 to 6 carbon atoms, and L represents a monoanionic ligand. When M represents iridium or rhodium, n is 2. When M represents platinum or palladium, n is 1.

One embodiment of the present invention is an organometallic complex represented by General Formula (G4).

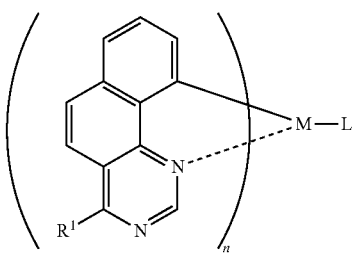

(G4)

In General Formula (G4), M represents iridium, platinum, palladium, or rhodium, $R^1$ represents a substituted or unsubstituted alkyl group having 1 to 6 carbon atoms, or a substituted or unsubstituted aryl group having 6 to 10 carbon atoms, and L represents a monoanionic ligand. When M represents iridium or rhodium, n is 2. When M represents platinum or palladium, n is 1.

In General Formulae (G3) and (G4), the monoanionic ligand is preferably a monoanionic bidentate chelate ligand with a beta-diketone structure or a monoanionic bidentate chelate ligand in which two coordinating elements are both nitrogen. A monoanionic bidentate chelate ligand having a beta-diketone structure is particularly preferable. A beta-diketone structure is preferably included for higher solubility of the organometallic complex in an organic solvent and easier purification. A beta-diketone structure is preferably included to obtain an organometallic complex with high emission efficiency. Furthermore, inclusion of a beta-diketone structure has advantages such as a higher sublimation property and excellent evaporativity.

In General Formulae (G3) and (G4), the monoanionic ligand is preferably represented by General Formula (L1) or (L2).

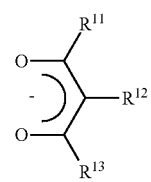

(L1)

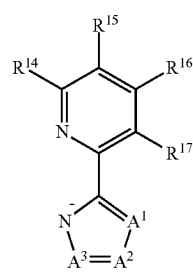

(L2)

$R^{11}$ to $R^{17}$ in General Formulae (L1) and (L2) separately represent hydrogen or a substituted or unsubstituted alkyl group having 1 to 6 carbon atoms, $A^1$ to $A^3$ separately represent nitrogen or carbon bonded to hydrogen or a substituent R. The substituent R represents an alkyl group having 1 to 6 carbon atoms or a phenyl group.

One embodiment of the present invention is an organometallic complex represented by General Formula (G5).

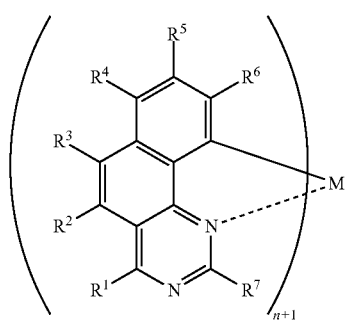

(G5)

In General Formula (G5), M represents iridium, platinum, palladium, or rhodium, $R^1$ represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms. When M represents iridium or rhodium, n is 2. When M represents platinum or palladium, n is 1.

One embodiment of the present invention is an organometallic complex represented by General Formula (G6).

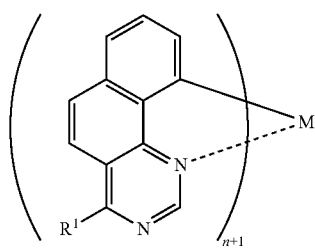

(G6)

In General Formula (G6), M represents iridium, platinum, palladium, or rhodium and $R^1$ represents a substituted or unsubstituted alkyl group having 1 to 6 carbon atoms, or a substituted or unsubstituted aryl group having 6 to 10 carbon atoms. When M represents iridium or rhodium, n is 2. When M represents platinum or palladium, n is 1.

When M in General Formula (G1) or (G2) represents rhodium, the organometallic complex with the structure represented by General Formula (G1) or (G2) has a molecular weight smaller than that when M represents iridium, platinum, or palladium. When M represents trivalent rhodium, the organometallic complex represented by any of General Formulae (G3) to (G6) has a molecular weight smaller than that when M represents trivalent iridium. When M represents platinum or palladium, n is 1, and thus the organometallic complex represented by any of General Formulae (G3) to (G6) has a molecular weight smaller than that when M represents iridium. The organometallic complex of one embodiment of the present invention can be deposited at a low evaporation temperature when having a small molecular weight.

<<Method for Synthesizing Benzoquinazoline Derivative Represented by General Formula (G0)>>

An example of a method for synthesizing a benzoquinazoline derivative represented by General Formula (G0) is described. The benzoquinazoline derivative represented by General Formula (G0) can be synthesized by the use of a chloride of substituted or unsubstituted benzoquinazoline.

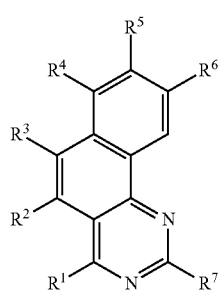

(G0)

In General Formula (G0), $R^1$ represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms.

The benzoquinazoline derivative represented by General Formula (G0) can be synthesized by simple Synthesis Scheme (A) as shown below.

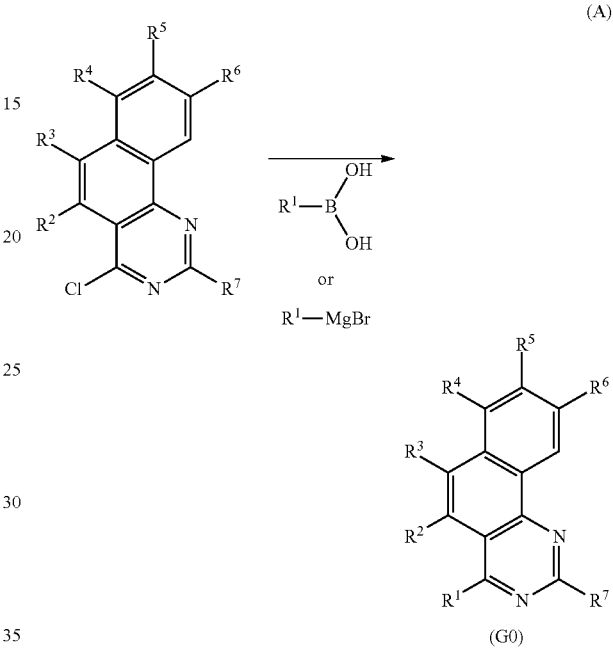

(A)

Various kinds of the chloride of substituted or unsubstituted benzoquinazoline as above described can be synthesized; accordingly, various kinds of the benzoquinazoline derivative represented by General Formula (G0) can also be synthesized. Thus, one of features of the organometallic complex of one embodiment of the present invention is the abundance of ligand variation.

The following shows examples of methods for synthesizing the organometallic complexes represented by General Formulae (G3) and (G5) by ortho-metalating a benzoquinazoline derivative represented by General Formula (G0).

<<Method for Synthesizing Organometallic Complex of One Embodiment of the Present Invention Represented by General Formula (G3)>>

As shown in Synthesis Scheme (B), the benzoquinazoline derivative represented by General Formula (G0) and a metal compound which contains halogen (e.g., palladium chloride, iridium chloride, iridium bromide, iridium iodide, or potassium tetrachloroplatinate) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more kinds of such alcohol-based solvents, whereby a dinuclear complex (P), which is one type of an organometallic complex including a halogen-bridged structure and is a novel substance, can be obtained.

In any of the synthesis methods described in this embodiment, there is no particular limitation on a heating method, and an oil bath, a sand bath, or an aluminum block may be used. Alternatively, microwaves can be used as a heating method.

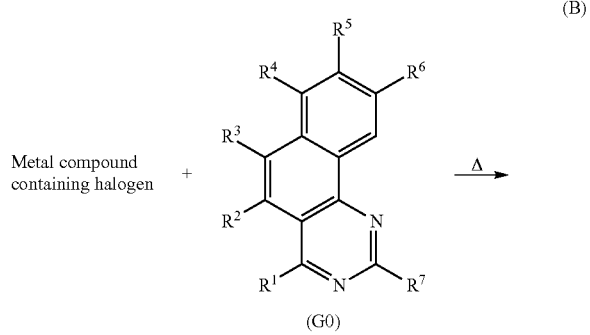

(B)

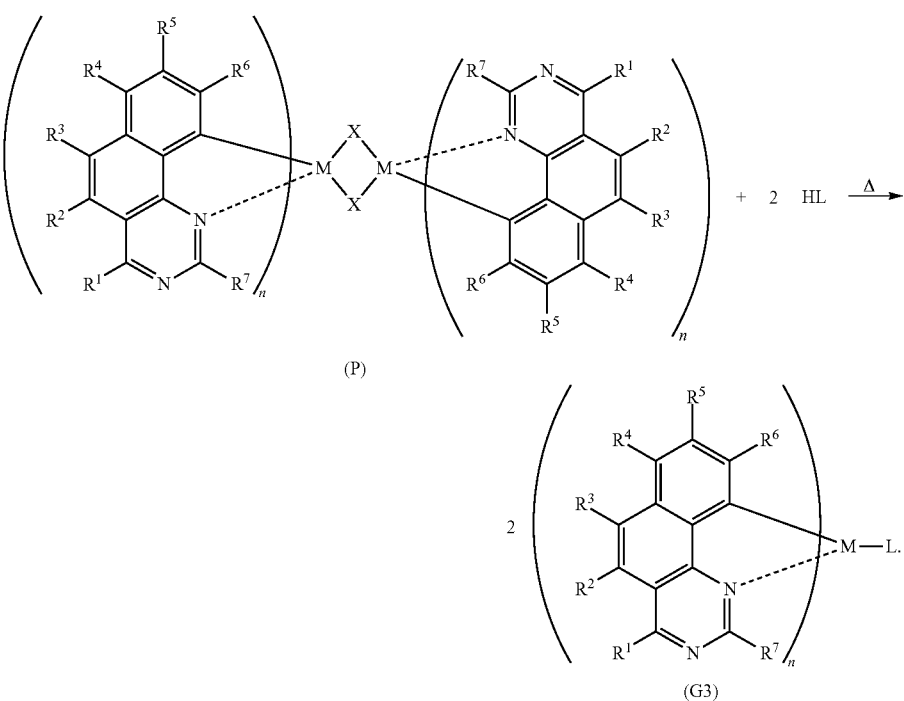

(P)

(C)

(G3)

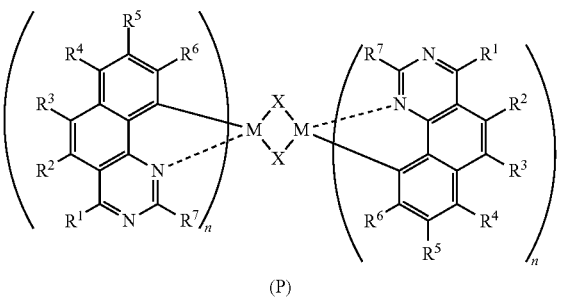

(P)

In Synthesis Scheme (B), X represents a halogen, M represents iridium, platinum, palladium, or rhodium, $R^1$ represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms. When M represents iridium or rhodium, n is 2. When M represents platinum or palladium, n is 1.

Furthermore, as shown in Synthesis Scheme (C), the dinuclear complex (P) obtained in Synthesis Scheme (B) is reacted with HL which is a material of a monoanionic ligand in an inert gas atmosphere, whereby a proton of HL is separated and L coordinates to the central metal M. Thus, the organometallic complex of one embodiment of the present invention which is represented by General Formula (G3) can be obtained.

In Synthesis Scheme (C), X represents a halogen, M represents iridium, platinum, palladium, or rhodium, L represents a monoanionic ligand, $R^1$ represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms. When M represents iridium or rhodium, n is 2. When M represents platinum or palladium, n is 1.

<<Method for Synthesizing Organometallic Complex of One Embodiment of the Present Invention Represented by General Formula (G5)>>

The organometallic complex of one embodiment of the present invention which is represented by General Formula (G5) can be synthesized according to Synthesis Scheme (D). Specifically, the benzoquinazoline derivative represented by General Formula (G0) is mixed with a metal compound which contains halogen (e.g., rhodium chloride hydrate, palladium chloride, iridium chloride, iridium bromide, iridium iodide, or potassium tetrachloroplatinate) or with an organometallic complex (e.g., an acetylacetonate complex or a diethylsulfide complex) and the mixture is then heated, so that the organometallic complex of one embodiment of the present invention represented by General Formula (G5) can be obtained. Further, this heating process may be performed after the benzoquinazoline derivative represented by General Formula (G0) and the metal compound which contains halogen or the organometallic complex are dissolved in an alcohol-based solvent (e.g., glycerol, ethylene glycol, 2-methoxyethanol, or 2-ethoxyethanol).

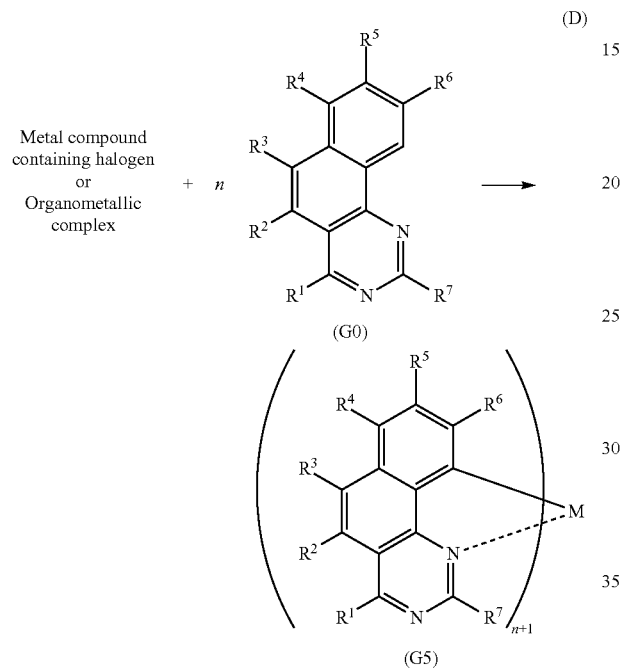

In Synthesis Scheme (D), M represents iridium, platinum, palladium, or rhodium, $R^1$ represents a substituted or unsubstituted alkyl group having 1 to 6 carbon atoms, or a substituted or unsubstituted aryl group having 6 to 10 carbon atoms, and $R^2$ to $R^7$ separately represent hydrogen or a substituted or unsubstituted alkyl group having 1 to 6 carbon atoms. When M represents iridium or rhodium, n is 2. When M represents platinum or palladium, n is 1.

Structural Formulae (100) to (120) are specific structural formulae of the organometallic complex of one embodiment of the present invention. Note that the present invention is not limited to these examples.

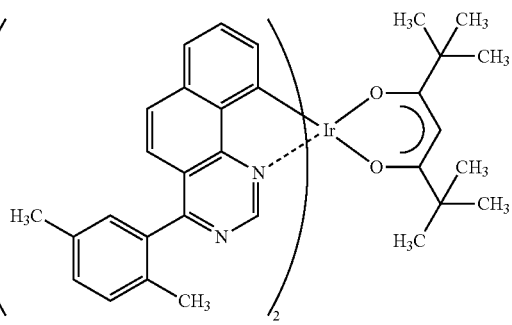

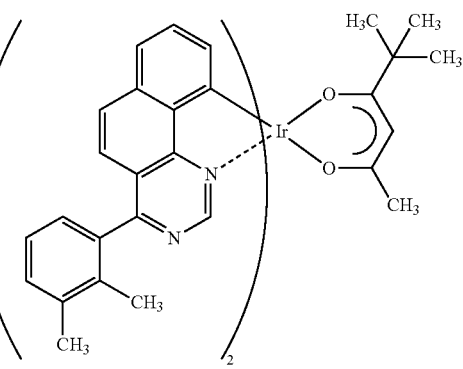

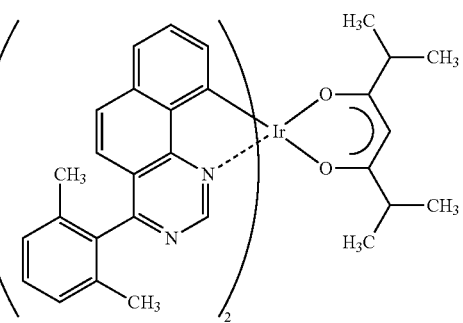

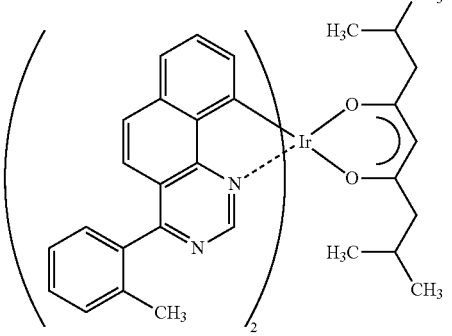

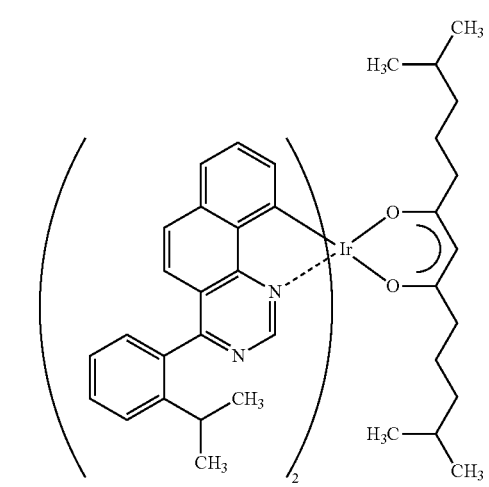
(105)
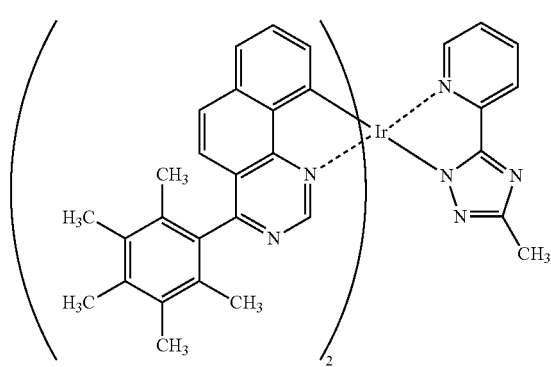
(106)
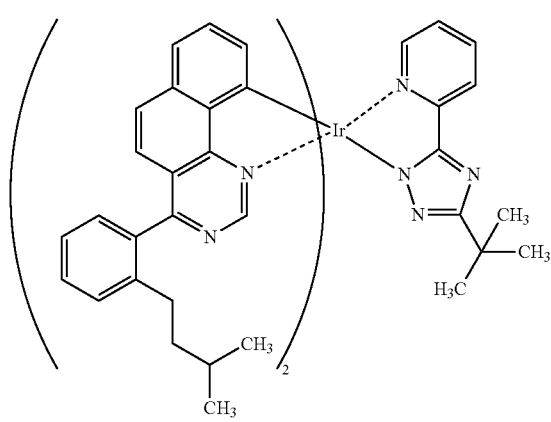
(107)
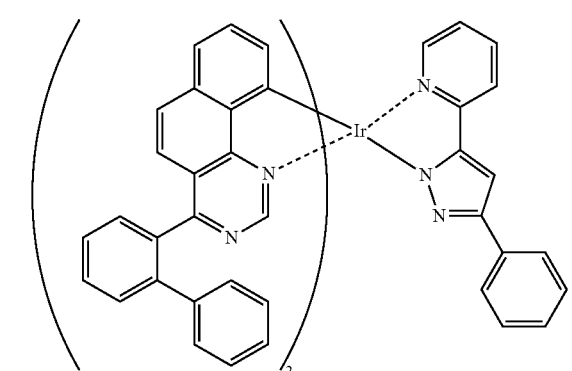
(108)
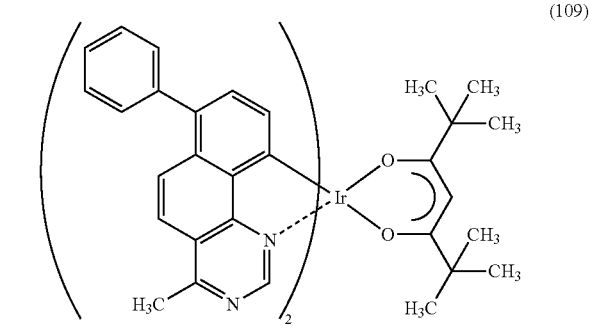
(109)
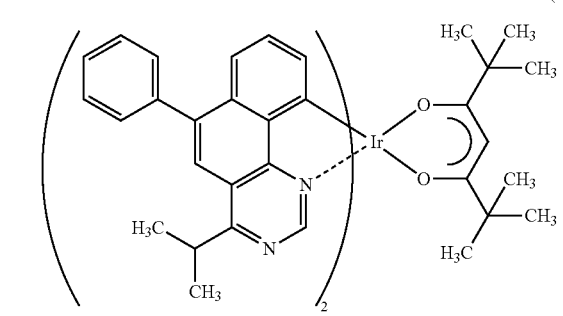
(110)
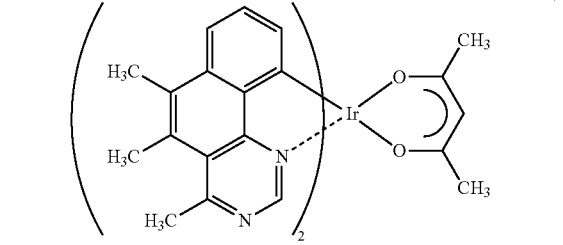
(111)
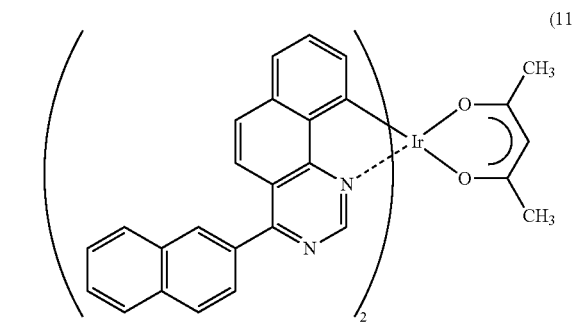
(112)

(113)
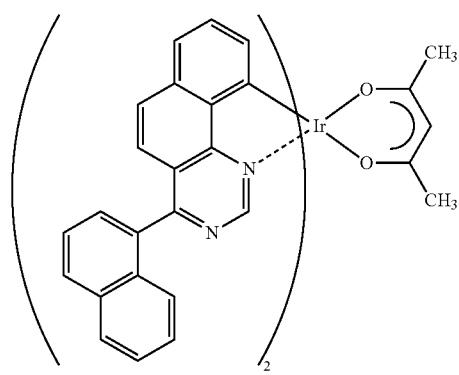

(114)
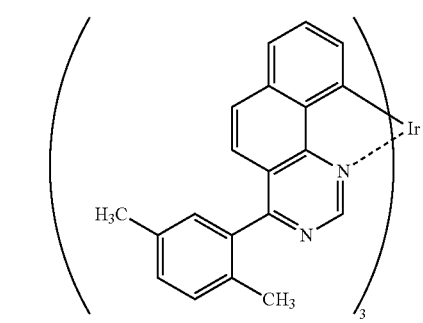

(115)
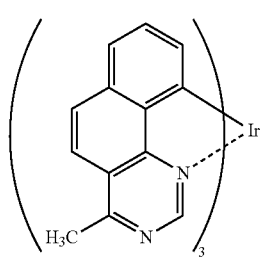

(116)
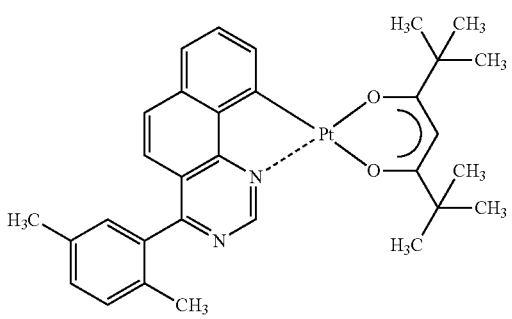

(117)
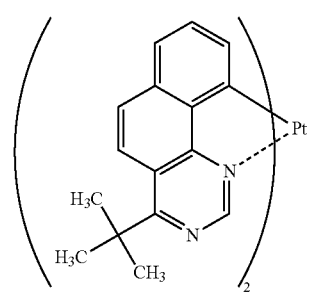

(118)
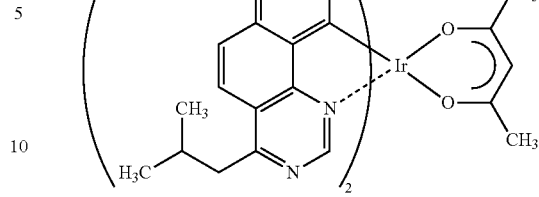

(119)
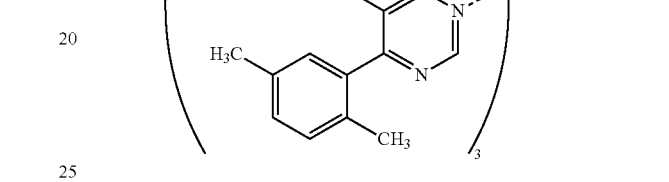

(120)
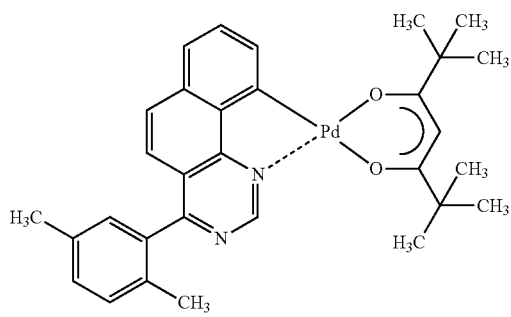

Depending on the type of the ligand, there can be stereoisomers of the organometallic complexes represented by Structural Formulae (100) to (120), and such isomers are also included in the category of the organometallic complex of one embodiment of the present invention.

Any of the above-described organometallic complexes of embodiments of the present invention can emit phosphorescence and has a broad emission spectrum in the wavelength range of red to yellowish green, and thus can be used as a light-emitting material or a light-emitting substance of a light-emitting element.

With the use of the organometallic complex of one embodiment of the present invention, a light-emitting element, a light-emitting device, an electronic device, or a lighting device with high emission efficiency can be provided. Alternatively, a light-emitting element, a light-emitting device, an electronic device, or a lighting device with low power consumption can be provided.

With the use of the organometallic complex of one embodiment of the present invention, a light-emitting element, a light-emitting device, an electronic device, or a lighting device with high reliability can be provided.

In this embodiment, any of the structures described in another embodiment can be used in appropriate combination.

Embodiment 2

In this embodiment, light-emitting elements of embodiments of the present invention will be described with reference to FIGS. 1A to 1D.

The light-emitting element of one embodiment of the present invention includes the organometallic complex of one embodiment of the present invention between a pair of electrodes. In this embodiment, a light-emitting element which includes, as a light-emitting substance, the organometallic complex containing at least any one of metals of iridium, platinum, palladium, and rhodium and a ligand with a benzoquinazoline skeleton is described.

<<Structural Example of Light-Emitting Element>>

A light-emitting element illustrated in FIG. 1A includes an EL layer 203 between a first electrode 201 and a second electrode 205. In this embodiment, the first electrode 201 serves as an anode, and the second electrode 205 serves as a cathode.

When a voltage higher than the threshold voltage of the light-emitting element is applied between the first electrode 201 and the second electrode 205, holes are injected to the EL layer 203 from the first electrode 201 side and electrons are injected to the EL layer 203 from the second electrode 205 side. The injected electrons and holes recombine in the EL layer 203 and a light-emitting substance contained in the EL layer 203 emits light.

The EL layer 203 includes at least a light-emitting layer 303 containing a light-emitting substance. In this embodiment, an example is described in which the light-emitting layer 303 contains, as a light-emitting substance, the organometallic complex of one embodiment of the present invention described in Embodiment 1.

Further, when a plurality of light-emitting layers are provided in the EL layer and emission colors of the light-emitting layers are made different, light emission of a desired color can be provided from the light-emitting element as a whole. For example, in a light-emitting element having two light-emitting layers, the emission colors of first and second light-emitting layers are complementary, so that the light-emitting element can emit white light as a whole. Note that the word "complementary" means color relationship in which an achromatic color is obtained when colors are mixed. In other words, when light components obtained from substances which emit light of complementary colors are mixed, white emission can be obtained. Further, the same applies to a light-emitting element having three or more light-emitting layers. Note that in the light-emitting element of one embodiment of the present invention which includes a plurality of light-emitting layers, at least one light-emitting layer contains the organometallic complex of one embodiment of the present invention, and all the light-emitting layers may contain the organometallic complex of one embodiment of the present invention.

In addition to the light-emitting layer, the EL layer 203 may further include one or more layers containing any of a substance with a high hole-injection property, a substance with a high hole-transport property, a substance with a high electron-transport property, a substance with a high electron-injection property, a substance with a bipolar property (a substance with a high electron-transport property and a high hole-transport property), and the like. For the EL layer 203, either a low molecular compound or a high molecular compound can be used, and an inorganic compound may also be used.

Figure 1B:
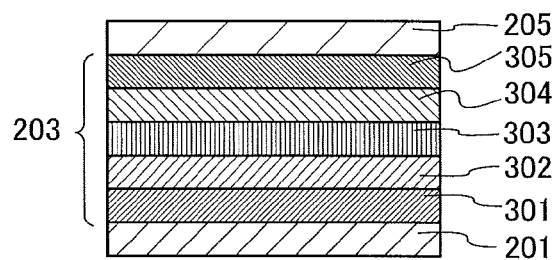

A light-emitting element illustrated in FIG. 1B includes the EL layer 203 between the first electrode 201 and the second electrode 205, and in the EL layer 203, a hole-injection layer 301, a hole-transport layer 302, the light-emitting layer 303, an electron-transport layer 304, and an electron-injection layer 305 are stacked in that order from the first electrode 201 side.

Figure 1C:
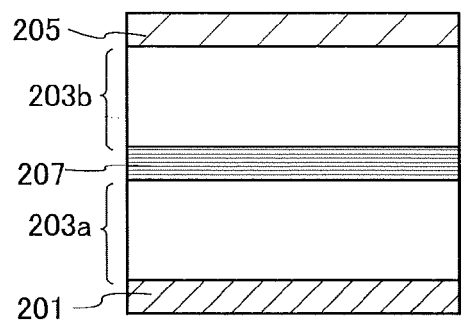
Figure 1D:
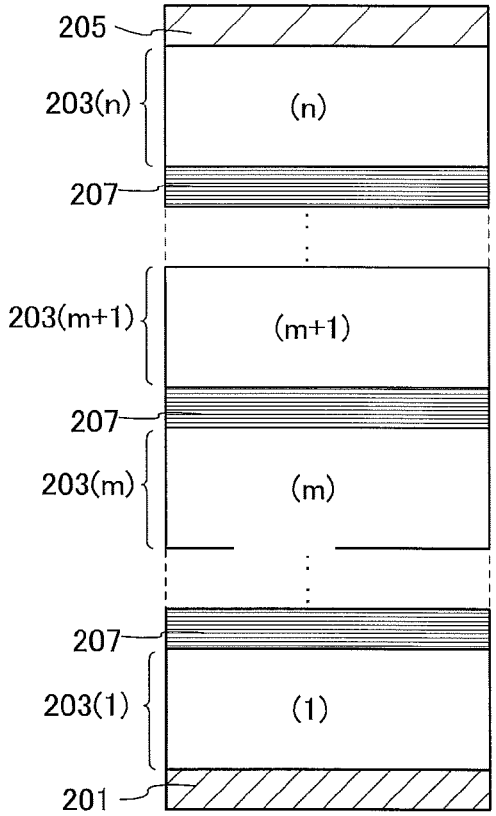

As in light-emitting elements illustrated in FIGS. 1C and 1D, a plurality of EL layers may be stacked between the first electrode 201 and the second electrode 205. In this case, an intermediate layer 207 is preferably provided between the stacked EL layers. The intermediate layer 207 includes at least a charge-generation region.

For example, the light-emitting element illustrated in FIG. 1C includes the intermediate layer 207 between a first EL layer 203a and a second EL layer 203b. The light-emitting element illustrated in FIG. 1D includes n EL layers (n is a natural number of 2 or more), and the intermediate layers 207 between the EL layers.

The following shows behaviors of electrons and holes in the intermediate layer 207 between the EL layer 203(m) and the EL layer 203(m+1). When a voltage higher than the threshold voltage of the light-emitting element is applied between the first electrode 201 and the second electrode 205, holes and electrons are generated in the intermediate layer 207, and the holes move into the EL layer 203(m+1) provided on the second electrode 205 side and the electrons move into the EL layer 203(m) provided on the first electrode 201 side. The holes injected into the EL layer 203(m+1) recombine with the electrons injected from the second electrode 205 side, so that a light-emitting substance contained in the EL layer 203(m+1) emits light. Further, the electrons injected into the EL layer 203(m) recombine with the holes injected from the first electrode 201 side, so that a light-emitting substance contained in the EL layer 203(m) emits light. Thus, the holes and electrons generated in the intermediate layer 207 cause light emission in the respective EL layers.

Note that the EL layers can be provided in contact with each other with no intermediate layer provided therebetween when these EL layers allow the same structure as the intermediate layer to be formed therebetween. For example, when the charge-generation region is formed over one surface of an EL layer, another EL layer can be provided in contact with the surface.

Further, by forming EL layers to emit light of different colors from each other, a light-emitting element as a whole can provide light emission of a desired color. For example, in a light-emitting element having two EL layers, the emission colors of first and second EL layers are complementary, so that the light-emitting element can emit white light as a whole. This can be applied to a light-emitting element having three or more EL layers.

<<Materials of Light-Emitting Element>>

Examples of materials which can be used for the layers are described below. Note that each layer is not limited to a single layer, and may be a stack including two or more layers.

<Anode>

The electrode serving as the anode (the first electrode 201 in this embodiment) can be formed using one or more kinds of conductive metals, alloys, conductive compounds, and the like. In particular, it is preferable to use a material with a high work function (4.0 eV or more). Examples include indium tin oxide (ITO), indium tin oxide containing silicon or silicon oxide, indium zinc oxide, indium oxide containing tungsten oxide and zinc oxide, graphene, gold, platinum, nickel, tungsten, chromium, molybdenum, iron, cobalt, copper, palladium, titanium, and a nitride of a metal material (e.g., titanium nitride).

When the anode is in contact with the charge-generation region, any of a variety of conductive materials can be used regardless of their work functions; for example, aluminum, silver, an alloy containing aluminum, or the like can be used.

<Cathode>

The electrode serving as the cathode (the second electrode 205 in this embodiment) can be formed using one or more kinds of conductive metals, alloys, conductive compounds, and the like. In particular, it is preferable to use a material with a low work function (3.8 eV or less). Examples include aluminum, silver, an element belonging to Group 1 or 2 of the periodic table (e.g., an alkali metal such as lithium or cesium, an alkaline earth metal such as calcium or strontium, or magnesium), an alloy containing any of these elements (e.g., Mg—Ag or Al—Li), a rare earth metal such as europium or ytterbium, and an alloy containing any of these rare earth metals.

Note that when the cathode is in contact with the charge-generation region, a variety of conductive materials can be used regardless of its work function. For example, ITO, indium tin oxide containing silicon or silicon oxide, or the like can be used.

The electrodes may be formed separately by a vacuum evaporation method or a sputtering method. Alternatively, when a silver paste or the like is used, a coating method or an inkjet method may be used.

<Light-Emitting Layer>

As already described above, the light-emitting element in this embodiment includes the light-emitting layer 303 which contains, as a light-emitting substance, the organometallic complex of one embodiment of the present invention described in Embodiment 1. The light-emitting layer may contain another compound in addition to the organometallic complex. The light-emitting element of one embodiment of the present invention may include a light-emitting layer containing another compound in addition to the light-emitting layer containing the organometallic complex. In that case, as the light-emitting substance, a fluorescent compound, a phosphorescent compound, a substance exhibiting thermally activated delayed fluorescence, or the like can be used.

The light-emitting substance (guest material) is preferably dispersed in the host material. When the light-emitting layer has the structure in which the guest material is dispersed in the host material, the crystallization of the light-emitting layer can be inhibited. Further, it is possible to inhibit concentration quenching due to high concentration of the guest material, and thus the light-emitting element can have higher emission efficiency. A compound to be described below which easily accepts electrons or a compound to be described below which easily accepts holes can be used as the host material.

Note that the $T_1$ level of the host material (or a material other than the guest material in the light-emitting layer) is preferably higher than the $T_1$ level of the guest material. This is because, when the $T_1$ level of the host material is lower than the $T_1$ level of the guest material, the triplet excitation energy of the guest material which is to contribute to light emission is quenched by the host material and accordingly the emission efficiency is decreased.

Here, for improvement in efficiency of energy transfer from a host material to a guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) have a large overlap with an absorption spectrum of a guest material (specifically, spectrum in an absorption band on the longest wavelength (lowest energy) side).

However, in general, it is difficult to obtain an overlap between a fluorescence spectrum of a host material and an absorption spectrum in an absorption band on the longest wavelength (lowest energy) side of a guest material. The reason for this is as follows. If the fluorescence spectrum of the host material overlaps with the absorption spectrum in the absorption band on the longest wavelength (lowest energy) side of the guest material, since a phosphorescence spectrum of the host material is located on a long wavelength (low energy) side as compared to the fluorescence spectrum, the $T_1$ level of the host material becomes lower than the $T_1$ level of the phosphorescent compound and the above-described problem of quenching occurs; yet, when the host material is designed such that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material to maximize energy transfer from a singlet excited state of the host material.

Thus, it is preferable that in the light-emitting layer of the light-emitting element of one embodiment of the present invention, a third substance be contained in addition to a phosphorescent compound and a host material (which are respectively regarded as a first substance and a second substance contained in the light-emitting layer), and a combination of the host material the third substance form an exciplex (also referred to as excited complex). In that case, the host material and the third substance form an exciplex at the time of recombination of carriers (electrons and holes) in the light-emitting layer. Thus, in the light-emitting layer, fluorescence spectra of the host material and the third substance are converted into an emission spectrum of the exciplex which is located on a longer wavelength side. Moreover, when the host material and the third substance are selected such that the emission spectrum of the exciplex has a large overlap with the absorption spectrum of the guest material, energy transfer from a singlet excited state can be maximized. Note that also in the case of a triplet excited state, energy transfer from the exciplex, not the host material, is assumed to occur. In one embodiment of the present invention to which such a structure is applied, energy transfer efficiency can be improved owing to energy transfer utilizing an overlap between an emission spectrum of an exciplex and an absorption spectrum of a phosphorescent compound; accordingly, a light-emitting element with high external quantum efficiency can be provided.

As the guest material, the organometallic complex of one embodiment of the present invention can be used. Although any combination of the host material and the third substance can be used as long as an exciplex is formed, a compound which easily accepts electrons (a compound having an electron-trapping property) and a compound which easily accepts holes (a compound having a hole-trapping property) are preferably combined.

Examples of a compound which easily accepts holes and which can be used as the host material or the third substance include a π-electron rich heteroaromatic compound (e.g., a carbazole derivative or an indole derivative) and an aromatic amine compound.

Specifically, the following examples can be given: 4-phenyl-4'-(9-phenyl-9H-carbazol-3-yl)triphenylamine (abbreviation: PCBA1BP), 4,4'-di(1-naphthyl)-4''-(9-phenyl-9H-carbazol-3-yl)triphenylamine (abbreviation: PCBNBB), 3-[N-(1-naphthyl)-N-(9-phenylcarbazol-3-yl)amino]-9-phenylcarbazole (abbreviation: PCzPCN1), 4,4',4''-tris[N-(1-naphthyl)-N-phenylamino]triphenylamine (abbreviation: 1'-TNATA), 2,7-bis[N-(4-diphenylaminophenyl)-N-phenylamino]spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-diphenylamino-9H-fluoren-7-yl)diphenylamine (abbreviation: DPNF), N,N',N''-triphenyl-N,N'',N''-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N-phenylamino]phenyl}-N-phenylamino)biphenyl (abbreviation: DNTPD), and 3,6-bis[N-(4-diphenylaminophenyl)-N-(1-naphthyl)amino]-9-phenylcarbazole (abbreviation: PCzTPN2).

The following examples can also be given: aromatic amine compounds such as 4,4'-bis[N-(1-naphthyl)-N-phenylamino]biphenyl (abbreviation: NPB or α-NPD), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), 4,4'-bis[N-(spiro-9,9'-bifluoren-2-yl)-N-phenylamino]biphenyl (abbreviation: BSPB), 4,4',4''-tris(N-carbazolyl)triphenylamine (abbreviation: TCTA), 4-phenyl-4'-(9-phenylfluoren-9-yl)triphenylamine (abbreviation: BPAFLP), and 4,4'-bis[N-(9,9-dimethylfluoren-2-yl)-N-phenylamino]biphenyl (abbreviation: DFLDPBi); and carbazole derivatives such as 4,4'-di(N-carbazolyl)biphenyl (abbreviation: CBP), 9-[4-(10-phenyl-9-anthracenyl)phenyl]-9H-carbazole (abbreviation: CzPA), and 9-phenyl-3-[4-(10-phenyl-9-anthryl)phenyl]-9H-carbazole (abbreviation: PCzPA). In addition, high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl] phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD) can be given.

Examples of the compound which easily accepts electrons and which can be used as the host material or the third substance include a π-electron deficient heteroaromatic compound such as a nitrogen-containing heteroaromatic compound, a metal complex having a quinoline skeleton or a benzoquinoline skeleton, and a metal complex having an oxazole-based ligand or a thiazole-based ligand.

Specific examples include the following: metal complexes such as bis(10-hydroxybenzo[h]quinolinato)beryllium (abbreviation: BeBq$_2$), bis(2-methyl-8-quinolinolato)(4-phenylphenolato)aluminum (abbreviation: BAlq), bis(8-quinolinolato)zinc(II) (abbreviation: Znq), bis[2-(2-hydroxyphenyl)benzoxazolato]zinc (abbreviation: Zn(BOX)$_2$), and bis[2-(2-hydroxyphenyl)benzothiazolato]zinc (abbreviation: Zn(BTZ)$_2$); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having quinoxaline skeletons or dibenzoquinoxaline skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), and 2-[3'-(9H-carbazol-9-yl)biphenyl-3-yl]dibenzo[f,h]quinoxaline (abbreviation: 2mCzBPDBq); heterocyclic compounds having diazine skeletons (pyrimidine skeletons or pyrazine skeletons), such as 4,6-bis[3-(phenanthren-9-yl)phenyl]pyrimidine (abbreviation: 4,6mPnP2Pm), 4,6-bis[3-(9H-carbazol-9-yl)phenyl]pyrimidine (abbreviation: 4,6mCzP2Pm), and 4,6-bis[3-(4-dibenzothienyl)phenyl]pyrimidine (abbreviation: 4,6mDBTP2Pm-II); heterocyclic compounds having pyridine skeletons, such as 3,5-bis[3-(9H-carbazol-9-yl)phenyl]pyridine (abbreviation: 35DCzPPy), 1,3,5-tri[3-(3-pyridyl)phenyl]benzene (abbreviation: TmPyPB), and 3,3',5,5'-tetra[(m-pyridyl)-phen-3-yl]biphenyl (abbreviation: BP4mPy). Among the above-described compounds, the heterocyclic compounds having quinoxaline skeletons or dibenzoquinoxaline skeletons, the heterocyclic compounds having diazine skeletons, and the heterocyclic compounds having pyridine skeletons have favorable reliability and can be preferably used.

The following examples can also be given: metal complexes having quinoline skeletons or benzoquinoline skeletons, such as tris(8-quinolinolato)aluminum (abbreviation: Alq) and tris(4-methyl-8-quinolinolato)aluminum (abbreviation: Almq$_3$); and heteroaromatic compounds such as bathophenanthroline (abbreviation: BPhen), bathocuproine (abbreviation: BCP), 3-(4-tert-butylphenyl)-4-(4-ethylphenyl)-5-(4-biphenylyl)-1,2,4-triazole (abbreviation: p-EtTAZ), and 4,4'-bis(5-methylbenzoxazol-2-yl)stilbene (abbreviation: BzOs). In addition, high molecular compounds such as poly(2,5-pyridinediyl) (abbreviation: PPy), poly[(9, 9-dihexylfluorene-2,7-diyl)-co-(pyridine-3,5-diyl)] (abbreviation: PF-Py) and poly[(9,9-dioctylfluorene-2,7-diyl)-co-(2,2'-bipyridine-6,6'-diyl)] (abbreviation: PF-BPy) can also be given.

The materials which can be used as the host material or the third substance are not limited to the above materials as long as a combination of the material used as the host material and the material used as the third substance can form an exciplex, an emission spectrum of the exciplex overlaps with an absorption spectrum of the guest material, and a peak of the emission spectrum of the exciplex is located on a longer wavelength side than a peak of the absorption spectrum of the guest material.

Note that when a compound which easily accepts electrons and a compound which easily accepts holes are used for the host material and the third substance, carrier balance can be controlled by the mixture ratio of the compounds. Specifically, the ratio of the host material to the third substance is preferably from 1:9 to 9:1.

Further, the exciplex may be focused at the interface between two layers. For example, when a layer containing the compound which easily accepts electrons and a layer containing the compound which easily accepts holes are stacked, the exciplex is formed in the vicinity of the interface thereof. These two layers may be used as the light-emitting layer in the light-emitting element of one embodiment of the present invention. In that case, the phosphorescent compound is added to the vicinity of the interface. The phosphorescent compound is added to one of the two layers or both.

<Hole-Transport Layer>

The hole-transport layer 302 contains a substance with a high hole-transport property.

The substance with a high hole-transport property is a substance with a property of transporting more holes than electrons, and is especially preferably a substance with a hole mobility of $10^{-6}$ cm$^2$/Vs or more.

For the hole-transport layer 302, it is possible to use any of the compounds which easily accept holes and are described as examples of the substance applicable to the light-emitting layer 303.

It is also possible to use an aromatic hydrocarbon compound such as 2-tert-butyl-9,10-di(2-naphthyl)anthracene (abbreviation: t-BuDNA), 9,10-di(2-naphthyl)anthracene (abbreviation: DNA), or 9,10-diphenylanthracene (abbreviation: DPAnth).

<Electron-Transport Layer>

The electron-transport layer 304 contains a substance with a high electron-transport property.

The substance with a high electron-transport property is an organic compound having a property of transporting more electrons than holes, and is especially preferably a substance with an electron mobility of $10^{-6}$ cm$^2$/Vs or more.

For the electron-transport layer 304, it is possible to use any of the compounds which easily accept electrons and are described as examples of the substance applicable to the light-emitting layer 303.

<Hole-Injection Layer>

The hole-injection layer 301 contains a substance with a high hole-injection property.

Examples of the substance with a high hole-injection property include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

A phthalocyanine-based compound such as phthalocyanine (abbreviation: H$_2$Pc), or copper(II) phthalocyanine (abbreviation: CuPc) can also be used.

Further alternatively, it is possible to use an aromatic amine compound which is a low molecular organic compound, such as TDATA, MTDATA, DPAB, DNTPD, 1,3,5-tris[N-(4-diphenylaminophenyl)-N-phenylamino]benzene (abbreviation: DPA3B), PCzPCA1, PCzPCA2, or PCzPCN1.

Further alternatively, it is possible to use a high molecular compound such as PVK, PVTPA, PTPDMA, or Poly-TPD, or a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS).

The hole-injection layer 301 may serve as the charge-generation region. When the hole-injection layer 301 in contact with the anode serves as the charge-generation region, any of a variety of conductive materials can be used for the anode regardless of their work functions. Materials contained in the charge-generation region will be described later.

<Electron-Injection Layer>

The electron-injection layer 305 contains a substance with a high electron-injection property.

Examples of the substance with a high electron-injection property include an alkali metal, an alkaline earth metal, a rare earth metal, and a compound thereof (e.g., an oxide thereof, a carbonate thereof, and a halide thereof), such as lithium, cesium, calcium, lithium oxide, lithium carbonate, cesium carbonate, lithium fluoride, cesium fluoride, calcium fluoride, and erbium fluoride.

The electron-injection layer 305 may serve as the charge-generation region. When the electron-injection layer 305 in contact with the cathode serves as the charge-generation region, any of a variety of conductive materials can be used for the cathode regardless of their work functions. Materials contained in the charge-generation region will be described later.

<Charge-Generation Region>

The charge-generation region may have either a structure in which an electron acceptor (acceptor) is added to an organic compound with a high hole-transport property or a structure in which an electron donor (donor) is added to an organic compound with a high electron-transport property. Alternatively, these structures may be stacked.

As examples of an organic compound with a high hole-transport property, the above materials which can be used for the hole-transport layer can be given, and as examples of an organic compound with a high electron-transport property, the above materials which can be used for the electron-transport layer can be given.

Further, as examples of the electron acceptor, 7,7,8,8-tetracyano-2,3,5,6-tetrafluoroquinodimethane (abbreviation: F4-TCNQ), chloranil, and the like can be given. In addition, transition metal oxides can be given. In addition, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable because it is stable in the air, has a low hygroscopic property, and is easily handled.

Further, as the electron donor, it is possible to use an alkali metal, an alkaline earth metal, a rare earth metal, a metal belonging to Group 2 or Group 13 of the periodic table, or an oxide or a carbonate thereof. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

The above-described layers included in the EL layer 203 and the intermediate layer 207 can be formed by any of the following methods: an evaporation method (including a vacuum evaporation method), a transfer method, a printing method, an inkjet method, a coating method, and the like.

By use of the light-emitting element described in this embodiment, a passive matrix light-emitting device or an active matrix light-emitting device in which driving of the light-emitting element is controlled by a transistor can be fabricated. Furthermore, the light-emitting device can be applied to an electronic device, a lighting device, or the like.

As described above, the light-emitting element of one embodiment of the present invention includes, between a pair of electrodes, an organometallic complex which contains at least any one of metals of iridium, platinum, palladium, and rhodium and a ligand with a benzoquinazoline skeleton. Thus, the light-emitting element can have high emission efficiency.

This embodiment can be freely combined with any of the other embodiments.

Embodiment 3

In this embodiment, a light-emitting device of one embodiment of the present invention will be described with reference to FIGS. 2A and 2B, FIGS. 3A to 3C, FIGS. 11A and 11B, FIGS. 12A and 12B, and FIGS. 13A to 13E. The light-emitting device of this embodiment includes the light-emitting element of one embodiment of the present invention. The light-emitting element has high emission efficiency and thus a light-emitting device with low power consumption can be obtained.

Figure 2A:
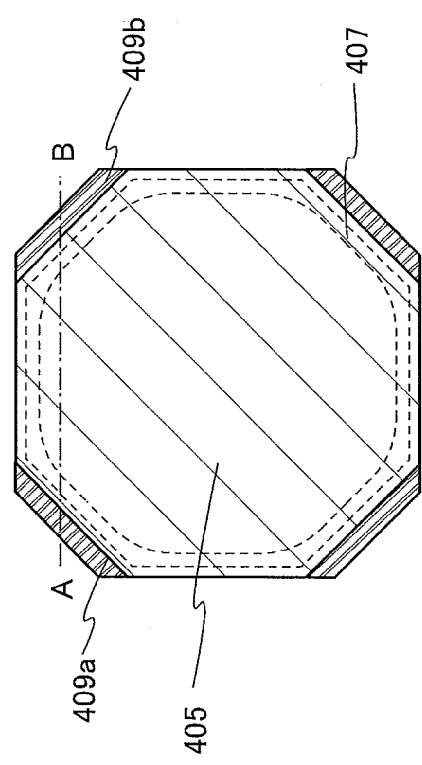
FIGS. 2A and 2B illustrate an example of a light-emitting device.
Figure 2B:
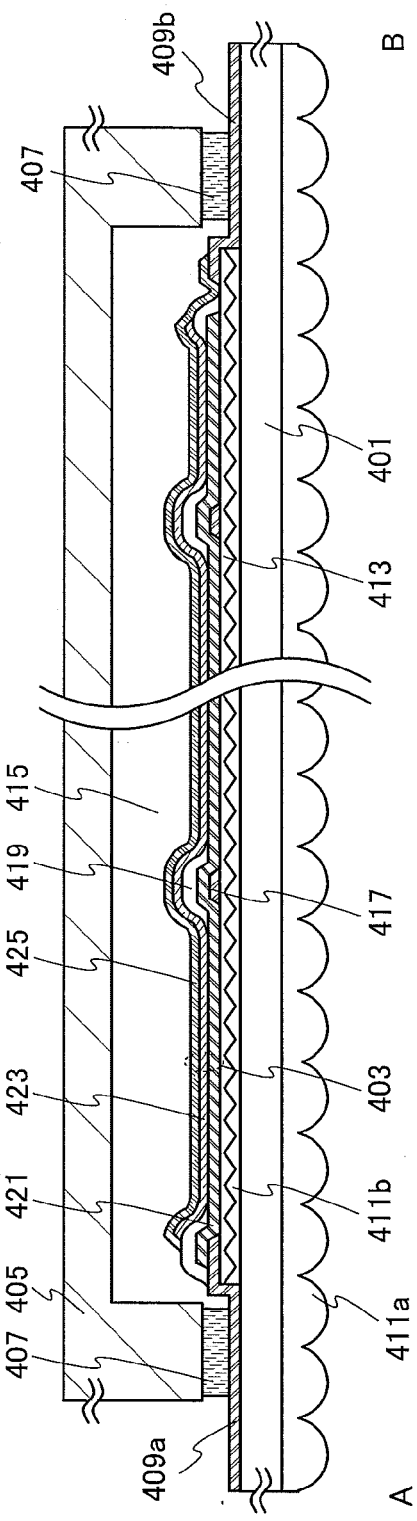

FIG. 2A is a plan view of the light-emitting device of one embodiment of the present invention, and FIG. 2B is a cross-sectional view taken along dashed-dotted line A-B in FIG. 2A.

In the light-emitting device illustrated in FIGS. 2A and 2B, a light-emitting element 403 is provided in a space 415 surrounded by a support substrate 401, a sealing substrate 405, and a sealing material 407. The light-emitting element 403 is an organic EL element having a bottom-emission structure; specifically, a first electrode 421 which transmits visible light is provided over the support substrate 401, an EL layer 423 is provided over the first electrode 421, and a second electrode 425 which reflects visible light is provided over the EL layer 423. The light-emitting element 403 is a light-emitting element to which one embodiment of the present invention is applied, and the EL layer 423 includes the organometallic complex containing at least any one of metals of iridium, platinum, palladium, and rhodium, and a ligand with a benzoquinazoline skeleton.

A first terminal 409a is electrically connected to an auxiliary wiring 417 and the first electrode 421. An insulating layer 419 is provided over the first electrode 421 in a region which overlaps with the auxiliary wiring 417. The first terminal 409a is electrically insulated from the second electrode 425 by the insulating layer 419. A second terminal 409b is electrically connected to the second electrode 425. Note that although the first electrode 421 is formed over the auxiliary wiring 417 in this embodiment, the auxiliary wiring 417 may be formed over the first electrode 421.

A light extraction structure 411a is preferably provided at the interface between the support substrate 401 and the atmosphere. When provided at the interface between the support substrate 401 and the atmosphere, the light extraction structure 411a can reduce light which cannot be extracted to the atmosphere due to total reflection, resulting in increased light extraction efficiency of the light-emitting device.

In addition, a light extraction structure 411b is preferably provided at the interface between the light-emitting element 403 and the support substrate 401. When the light extraction structure 411b has unevenness, a planarization layer 413 is preferably provided between the light extraction structure 411b and the first electrode 421. Accordingly, the first electrode 421 can be a flat film, and generation of leakage current in the EL layer 423 due to the unevenness of the first electrode 421 can be prevented. Further, because of the light extraction structure 411b at the interface between the planarization layer 413 and the support substrate 401, light which cannot be extracted to the atmosphere due to total reflection can be reduced, so that the light extraction efficiency of the light-emitting device can be increased.

As a material of the light extraction structure 411a and the light extraction structure 411b, a resin can be used, for example. Alternatively, for the light extraction structure 411a and the light extraction structure 411b, a hemispherical lens, a micro lens array, a film provided with an uneven surface structure, a light diffusing film, or the like can be used. For example, the light extraction structure 411a and the light extraction structure 411b can be formed by attaching the lens or film to the support substrate 401 with an adhesive or the like which has substantially the same refractive index as the support substrate 401 or the lens or film.

The surface of the planarization layer 413 which is in contact with the first electrode 421 is flatter than the surface of the planarization layer 413 which is in contact with the light extraction structure 411b. As a material of the planarization layer 413, a material with a light-transmitting property and a high refractive index (e.g., glass, a resin, or a liquid substance such as a refractive index liquid) can be used.

Figure 3A:
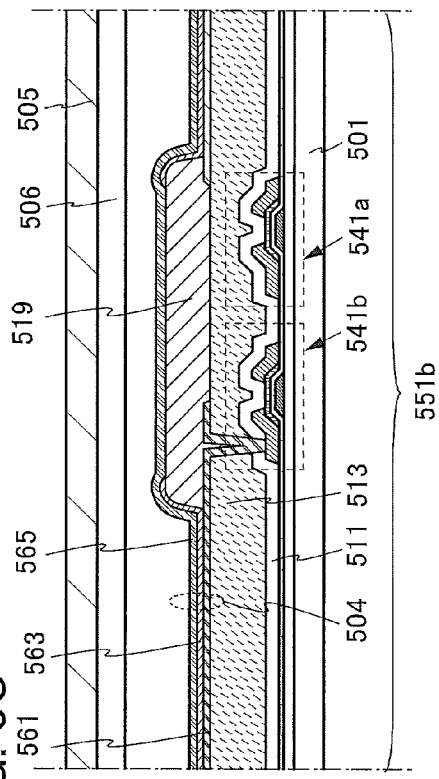
FIGS. 3A to 3C illustrate examples of a light-emitting device.
Figure 3C:
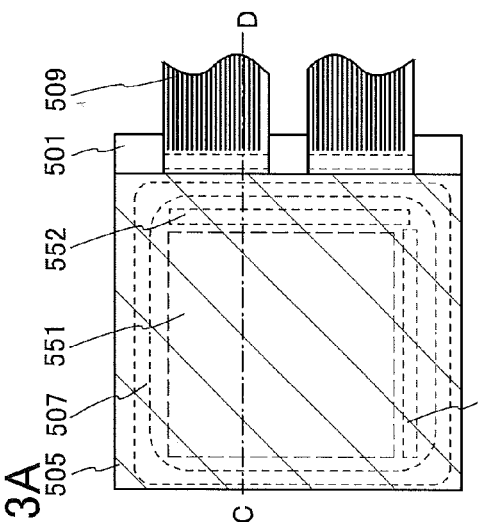
Figure 3B:
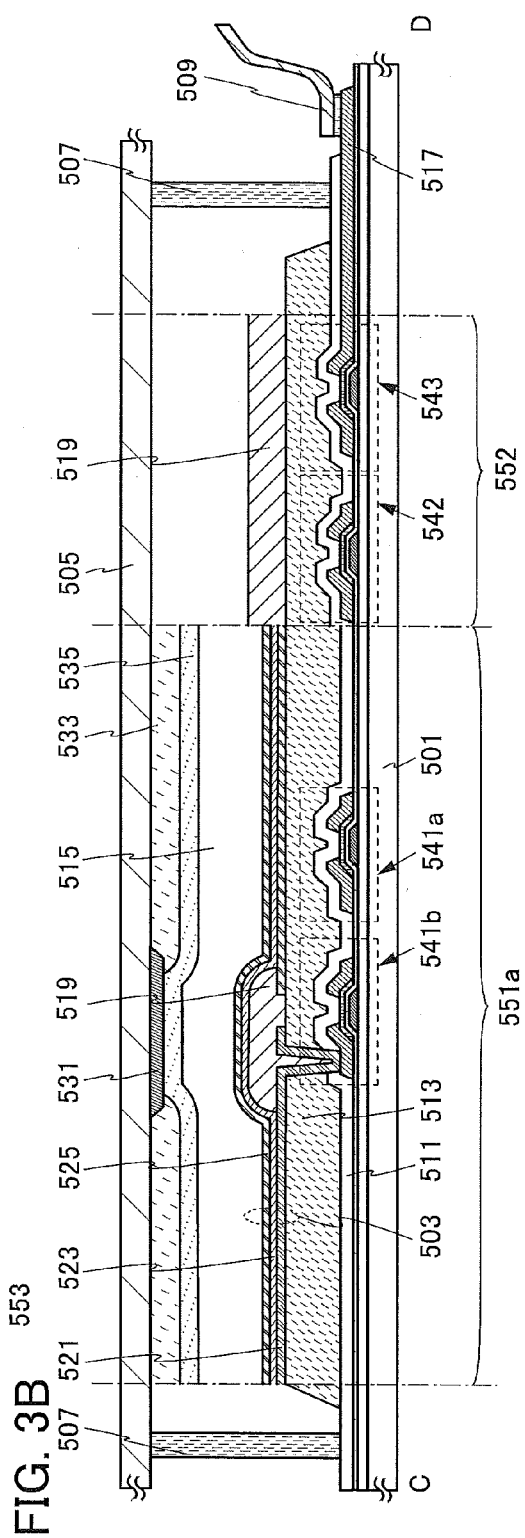

FIG. 3A is a plan view of a light-emitting device of one embodiment of the present invention, FIG. 3B is a cross-sectional view taken along dashed-dotted line C-D in FIG. 3A, and FIG. 3C is a cross-sectional view illustrating a variation of the light-emitting portion.

The active matrix light-emitting device illustrated in FIGS. 3A to 3C includes, over a support substrate 501, a light-emitting portion 551 (the cross section of which is illustrated in FIG. 3B and FIG. 3C as a light-emitting portion 551a and a light-emitting portion 551b, respectively), a driver circuit portion 552 (gate side driver circuit portion), a driver circuit portion 553 (source side driver circuit portion), and a sealing material 507. The light-emitting portion 551 and the driver circuit portions 552 and 553 are sealed in a space 515 surrounded by the support substrate 501, a sealing substrate 505, and the sealing material 507. Note that an on-cell touch sensor may be provided by forming a transparent conductive film on an outer surface of the sealing substrate 505 (a surface which does not face the supporting substrate 501) when the light-emitting device has a top-emission structure, or by forming a transparent conductive film on an outer surface of the supporting substrate 501 (a surface which does not face the sealing substrate 505) when the light-emitting device has a bottom-emission structure.

Any of a separate coloring method, a color filter method, and a color conversion method can be applied to the light-emitting device of one embodiment of the present invention. The light-emitting portion 551a of the light-emitting device which is fabricated by a color filter method is illustrated in FIG. 3B, and the light-emitting portion 551b of the light-emitting device which is fabricated by a separate coloring method is illustrated in FIG. 3C. The light-emitting portions each include a light-emitting element to which one embodiment of the present invention is applied, and an EL layer of the light-emitting element includes the organometallic complex containing at least any one of metals of iridium, platinum, palladium, and rhodium and a ligand with a benzoquinazoline skeleton.

Each of the light-emitting portion 551a and the light-emitting portion 551b includes a plurality of light-emitting units each including a switching transistor 541a, a current control transistor 541b, and a second electrode 525 electrically connected to a wiring (a source electrode or a drain electrode) of the current control transistor 541b.

A light-emitting element 503 included in the light-emitting portion 551a has a bottom-emission structure and includes a first electrode 521 which transmits visible light, an EL layer 523, and the second electrode 525. Further, a partition 519 is formed so as to cover an end portion of the first electrode 521.

A light-emitting element 504 included in the light-emitting portion 551b has a top-emission structure and includes a first electrode 561, an EL layer 563, and the second electrode 565 which transmits visible light. Further, the partition 519 is formed so as to cover an end portion of the first electrode 561. In the EL layer 563, at least layers (e.g., light-emitting layers) which contain different materials depending on the light-emitting element are colored separately.

Over the support substrate 501, a lead wiring 517 for connecting an external input terminal through which a signal (e.g., a video signal, a clock signal, a start signal, or a reset signal) or a potential from the outside is transmitted to the driver circuit portion 552 or 553 is provided. Here, an example is described in which a flexible printed circuit (FPC) 509 is provided as the external input terminal.

The driver circuit portions 552 and 553 include a plurality of transistors. FIG. 3B illustrates two of the transistors in the driver circuit portion 552 (transistors 542 and 543).

To prevent an increase in the number of fabrication steps, the lead wiring 517 is preferably formed using the same material and the same step(s) as those of the electrode or the wiring in the light-emitting portion or the driver circuit portion. Described in this embodiment is an example in which the lead wiring 517 is formed using the same material and the same step(s) as those of the source electrodes and the drain electrodes of the transistors included in the light-emitting portion 551 and the driver circuit portion 552.

In FIG. 3B, the sealing material 507 is in contact with a first insulating layer 511 over the lead wiring 517. The adhesion of the sealing material 507 to metal is low in some cases. Therefore, the sealing material 507 is preferably in contact with an inorganic insulating film over the lead wiring 517. Such a structure enables a light-emitting device to have high sealing capability, high adhesion, and high reliability. Examples of the inorganic insulating film include oxide films of metals and semiconductors, nitride films of metals and semiconductors, and oxynitride films of metals and semiconductors, and specifically, a silicon oxide film, a silicon nitride film, a silicon oxynitride film, a silicon nitride oxide film, an aluminum oxide film, a titanium oxide film, and the like.

The first insulating layer 511 prevents diffusion of impurities into a semiconductor included in the transistor. As the second insulating layer 513, an insulating film having a planarization function is preferably selected in order to reduce surface unevenness due to the transistor.

There is no particular limitation on the structure and materials of the transistor used in the light-emitting device of one embodiment of the present invention. A top-gate transistor may be used, or a bottom-gate transistor such as an inverted staggered transistor may be used. The transistor may be a channel-etched transistor or a channel-protective transistor. An n-channel transistor may be used and a p-channel transistor may also be used.

A semiconductor layer can be formed using silicon or an oxide semiconductor. Note that the transistor is preferably formed using an oxide semiconductor which is an In—Ga—Zn-based metal oxide for a semiconductor layer so as to have low off-state current, in which case an off-state leakage current of the light-emitting element can be reduced.

The sealing substrate 505 illustrated in FIG. 3B is provided with a color filter 533 as a coloring layer at a position overlapping with the light-emitting element 503 (a light-emitting region thereof), and is also provided with a black matrix 531 at a position overlapping with the partition 519. Further, an overcoat layer 535 is provided so as to cover the color filter 533 and the black matrix 531. The sealing substrate 505 illustrated in FIG. 3C is provided with a desiccant 506.

Figure 11A:
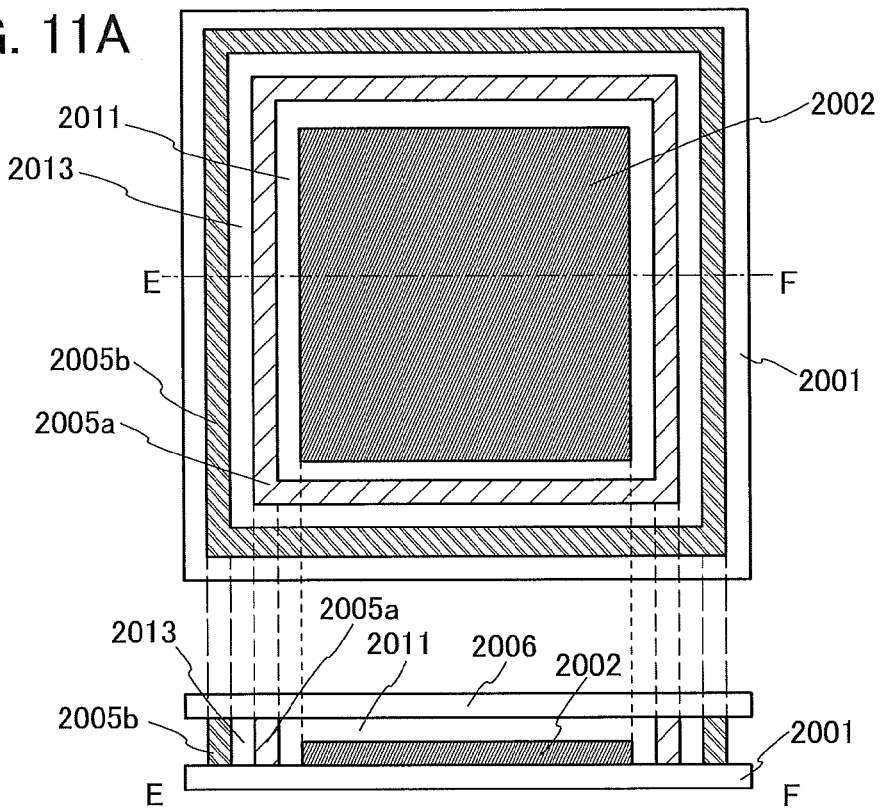
FIGS. 11A and 11B illustrate examples of a light-emitting device.
Figure 11B:
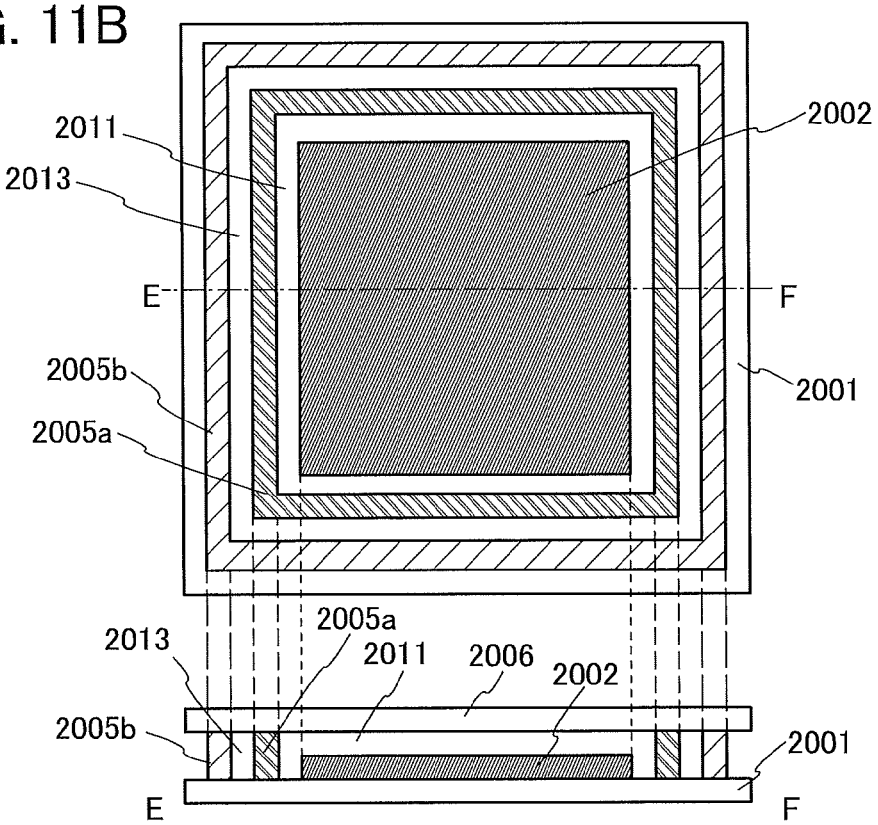

FIG. 11A is a plan view of a light-emitting device of one embodiment of the present invention, and FIG. 11B is a cross-sectional view taken along dashed-dotted line E-F in FIG. 11A.

The light-emitting device illustrated in FIG. 11A includes a light-emitting portion 2002 including a light-emitting element over a first substrate 2001. The light-emitting device has a structure in which a first sealant 2005a is provided so as to surround the light-emitting portion 2002 and a second sealant 2005b is provided so as to surround the first sealant 2005a (i.e., a double sealing structure). The light-emitting portion 2002 includes a light-emitting element to which one embodiment of the present invention is applied, and an EL layer of the light-emitting element includes the organometallic complex containing at least any one of metals of iridium, platinum, palladium, and rhodium, and a ligand with a benzoquinazoline skeleton.

Thus, the light-emitting portion 2002 is positioned in a space surrounded by the first substrate 2001, the second substrate 2006, and the first sealant 2005a.

Note that in this specification, the first sealant 2005a and the second sealant 2005b are not necessarily in contact with the first substrate 2001 and the second substrate 2006. For example, the first sealant 2005a may be in contact with an insulating film or a conductive film formed over the first substrate 2001.

In the above structure, the first sealant 2005a is a resin layer containing a desiccant, and the second sealant 2005b is a glass layer. This structure can increase an effect of inhibiting entry of impurities such as moisture and oxygen from the outside (hereinafter also referred to as a sealing property).

The first sealant 2005a is the resin layer, whereby the glass layer that is the second sealant 2005b can be prevented from having breaking or cracking (hereinafter also collectively referred to as a crack). Further, in the case where the sealing property of the second sealant 2005b is not sufficient, even when impurities such as moisture and oxygen enter a first space 2013, entry of the impurities such as moisture and oxygen into a second space 2011 can be inhibited owing to a high sealing property of the first sealant 2005a. Thus, deterioration of an organic compound, a metal material, and the like contained in the light-emitting element because of entry of impurities such as moisture and oxygen into the light-emitting portion 2002 can be inhibited.

In addition, the structure illustrated in FIG. 11B can be employed: the first sealant 2005a is a glass layer and the second sealant 2005b is a resin layer containing a desiccant.

In each of the light-emitting devices, distortion due to external force or the like increases toward the outer portion of the light-emitting device. In view of the above, the first sealant 2005a which has relatively small distortion due to external force or the like is a glass layer and the second sealant 2005b is a resin layer which has excellent impact resistance and excellent heat resistance and is not easily broken by deformation due to external force or the like, whereby entry of moisture and oxygen into the first space 2013 can be inhibited.

In addition to the above structure, a material serving as a desiccant may be contained in each of the first space 2013 and the second space 2011.

In the case where the first sealant 2005a or the second sealant 2005b is a glass layer, for example, a glass frit or a glass ribbon can be used. Note that at least a glass material is contained in a glass frit or a glass ribbon.

Further, in the case where a glass layer is formed using a glass frit, for example, a frit paste is applied to a substrate and is subjected to heat treatment, laser light irradiation, or the like. The frit paste contains a glass material, an organic solvent, a binder (e.g., a resin), and the like. The frit paste can be formed using any of a variety of materials and any of a variety of compositions. An absorber which absorbs light having a wavelength of laser light may be added to the fit material. For example, an Nd:YAG laser or a semiconductor laser is preferably used as a laser. The shape of laser light may be circular or quadrangular.

Note that the thermal expansion coefficient of the glass layer to be formed is preferably close to that of the substrate. The closer the thermal expansion coefficients are, the more generation of a crack in the glass layer or the substrate due to thermal stress can be inhibited.

Although any of a variety of materials, for example, photocurable resins such as an ultraviolet curable resin and thermosetting resins can be used in the case where the first sealant 2005a or the second sealant 2005b is a resin layer, it is particularly preferable to use a material which does not transmit moisture or oxygen. In particular, a photocurable resin is preferably used. The light-emitting element contains a material having low heat resistance in some cases. A photocurable resin, which is cured by light irradiation, is preferably used, in which case change in film quality and deterioration of an organic compound itself caused by heating of the light-emitting element can be inhibited.

As the desiccant contained in the resin layer, the first space 2013, or the second space 2011, any of a variety of materials can be used. As the desiccant, a substance which adsorbs moisture and the like by chemical adsorption or a substance which adsorbs moisture and the like by physical adsorption can be used. Examples thereof are alkali metal oxides, alkaline earth metal oxide (e.g., calcium oxide and barium oxide), sulfate, metal halides, perchlorate, zeolite, silica gel, and the like.

One or both of the first space 2013 and the second space 2011 may have, for example, an inert gas such as a rare gas or a nitrogen gas or may contain an organic resin. Note that these spaces are each in an atmospheric pressure state or a reduced pressure state.

As described above, the light-emitting device of one embodiment of the present invention has a double sealing structure, in which one of the first sealant 2005a and the second sealant 2005b is the glass layer having excellent productivity and an excellent sealing property, and the other is the resin layer which is hardly broken because of external force or the like, and can contain the desiccant inside, so that a sealing property of inhibiting entry of impurities such as moisture and oxygen from the outside can be improved.

Thus, the use of the structure described in this embodiment can provide a light-emitting device in which deterioration of a light-emitting element due to impurities such as moisture and oxygen is inhibited.

Figure 12A:
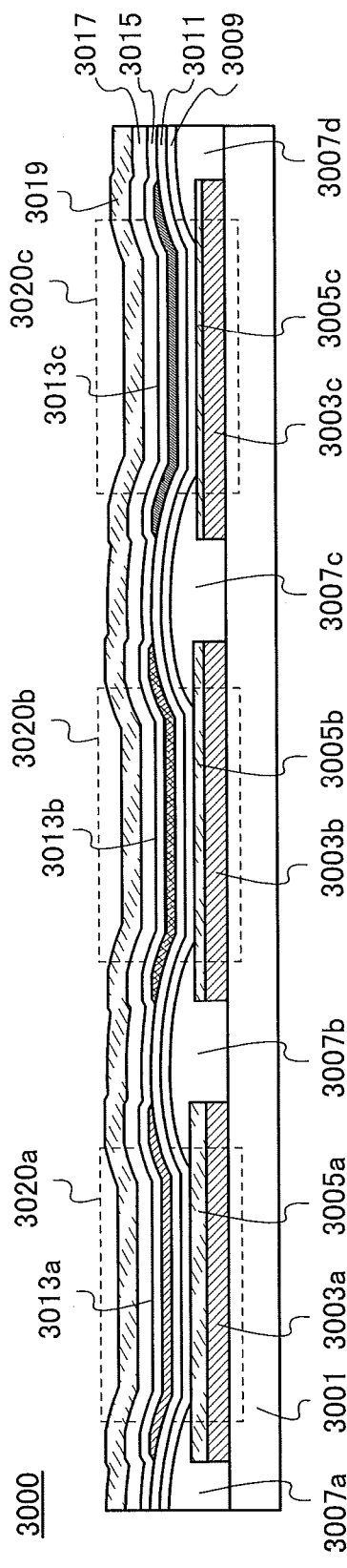
FIGS. 12A and 12B illustrate examples of a light-emitting device.
Figure 12B:
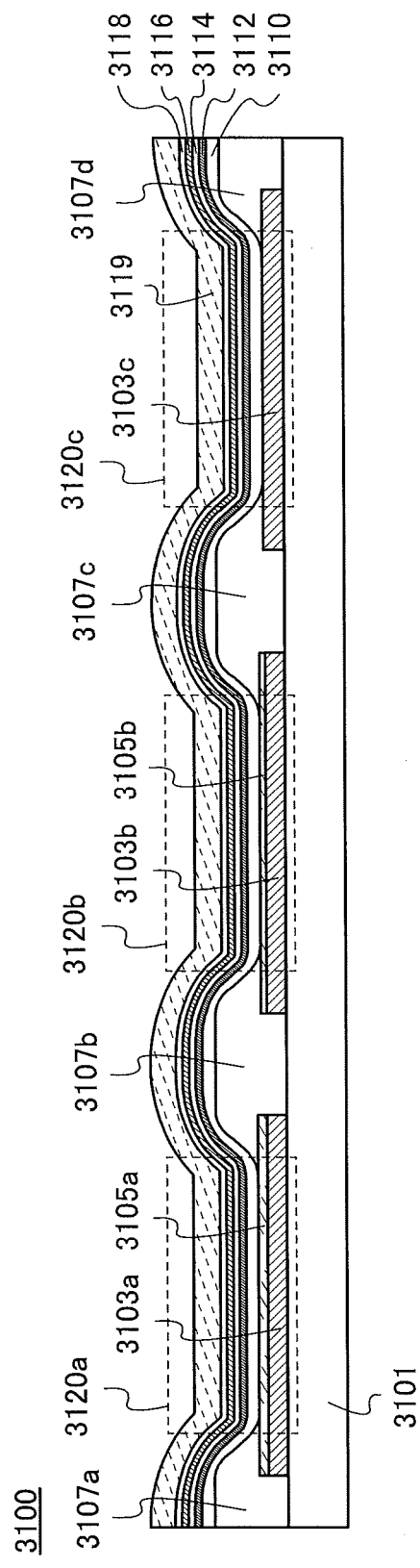

FIGS. 12A and 12B are cross-sectional views illustrating light-emitting devices of embodiments of the present invention. The light-emitting devices illustrated in FIGS. 12A and 12B each include a plurality of light-emitting elements.

A light-emitting device 3000 illustrated in FIG. 12A includes light-emitting elements 3020a, 3020b, and 3020c.

The light-emitting device 3000 includes island-shaped lower electrodes 3003a, 3003b, and 3003c over a substrate 3001. The lower electrodes 3003a, 3003b, and 3003c can function as anodes of the respective light-emitting elements. Reflective electrodes may be provided under the lower electrodes 3003a, 3003b, and 3003c. Transparent conductive layers 3005a, 3005b, and 3005c may be provided over the lower electrodes 3003a, 3003b, and 3003c, respectively. The transparent conductive layers 3005a, 3005b, and 3005c preferably have different thicknesses depending on an emission color of the element.

Further, the light-emitting device 3000 includes partitions 3007a, 3007b, 3007c, and 3007d, which are provided between the lower electrodes 3003a, 3003b, and 3003c.

Further, the light-emitting device 3000 includes a hole-injection layer 3009 over the lower electrodes 3003a, 3003b, and 3003c and the partitions 3007a, 3007b, 3007c, and 3007d. Further, the light-emitting device 3000 includes a hole-transport layer 3011 over the hole-injection layer 3009. The light-emitting device 3000 also includes light-emitting layers 3013a, 3013b, and 3013c over the hole-transport layer 3011. At least one of the light-emitting layers 3013a, 3013b, and 3013c includes the organometallic complex containing at least any one of metals of iridium, platinum, palladium, and rhodium, and a ligand with a benzoquinazoline skeleton.

The light-emitting device 3000 also includes an electron-transport layer 3015 over the light-emitting layers 3013a, 3013b, and 3013c. Further, the light-emitting device 3000 includes an electron-injection layer 3017 over the electron-transport layer 3015. The light-emitting device 3000 also includes an upper electrode 3019 over the electron-injection layer 3017. The upper electrode 3019 can function as cathodes of the light-emitting elements.

Note that although an example in which the lower electrodes 3003a, 3003b, and 3003c function as the anodes of the light-emitting elements and the upper electrode 3019 functions as the cathodes of the light-emitting elements is described with reference to FIG. 12A, the stacking order of the anode and the cathode may be switched. In this case, the stacking order of the electron-injection layer, the electron-transport layer, the hole-transport layer, and the hole-injection layer may be changed as appropriate.

A light-emitting device 3100 illustrated in FIG. 12B includes light-emitting elements 3120a, 3120b, and 3120c. The light-emitting elements 3120a, 3120b, and 3120c are tandem light-emitting elements in which a plurality of light-emitting layers are provided between lower electrodes 3103a, 3103b, and 3103c and an upper electrode 3119.

The light-emitting device 3100 includes the island-shaped lower electrodes 3103a, 3103b, and 3103c over a substrate 3101. The lower electrodes 3103a, 3103b, and 3103c can function as anodes of the light-emitting elements. Transparent conductive layers 3105a and 3105b may be provided over the lower electrodes 3103a and 3103b, respectively. The transparent conductive layers 3105a and 3105b preferably have different thicknesses depending on an emission color of the element. Although not illustrated, a transparent conductive layer may also be provided over the lower electrode 3103c.

Further, the light-emitting device 3100 includes partitions 3107a, 3107b, 3107c, and 3107d, which are provided between the lower electrodes 3103a, 3103b, and 3103c.

Further, the light-emitting device 3100 includes a hole-injection and hole-transport layer 3110 over the lower electrodes 3103a, 3103b, and 3103c and the partitions 3107a, 3107b, 3107c, and 3107d.

Further, the light-emitting device 3100 includes a first light-emitting layer 3112 over the hole-injection and hole-transport layer 3110. The light-emitting device 3100 also includes a second light-emitting layer 3116 over the first light-emitting layer 3112 with a charge-generation layer 3114 therebetween. At least one of the first light-emitting layer 3112 and the second light-emitting layer 3116 includes the organometallic complex containing at least any one of metals of iridium, platinum, palladium, and rhodium, and a ligand with a benzoquinazoline skeleton.

Further, the light-emitting device 3100 includes an electron-transport and electron-injection layer 3118 over the second light-emitting layer 3116. In addition, the light-emitting device 3100 includes the upper electrode 3119 over the electron-transport and electron-injection layer 3118. The upper electrode 3119 can function as cathodes of the light-emitting elements.

Note that although an example in which the lower electrodes 3103a, 3103b, and 3103c function as the anodes of the light-emitting elements and the upper electrode 3119 functions as the cathodes of the light-emitting elements is described with reference to FIG. 12B, the stacking order of the anode and the cathode may be switched. In this case, the stacking order of the electron-injection layer, the electron-transport layer, the hole-transport layer, and the hole-injection layer may be changed as appropriate.

Figure 13A:
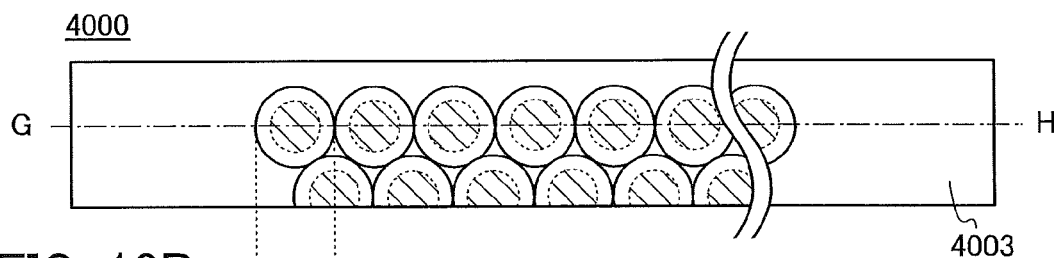
FIGS. 13A to 13E illustrate examples of a light-emitting device.
Figure 13B:
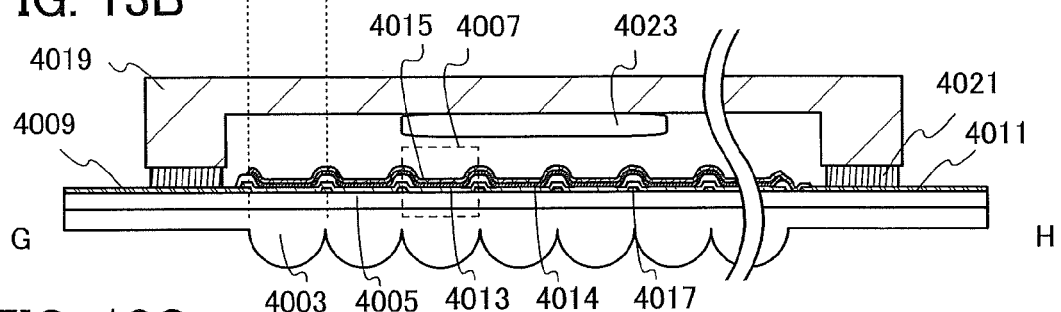
Figure 13C:
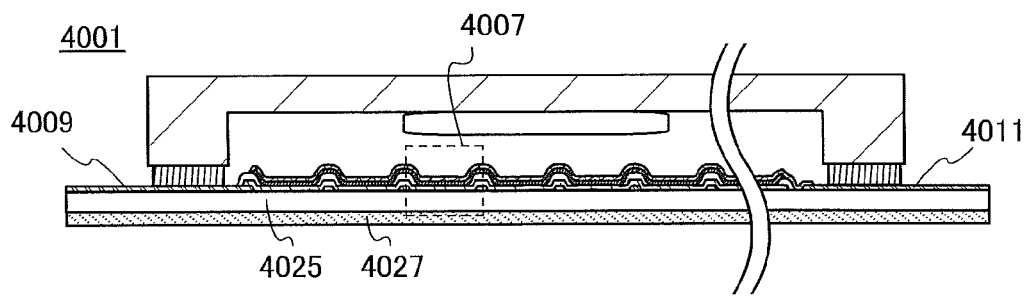
Figure 13D:
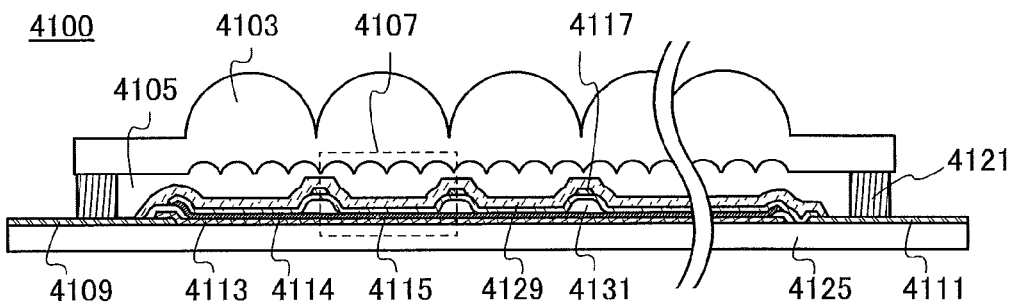
Figure 13E:
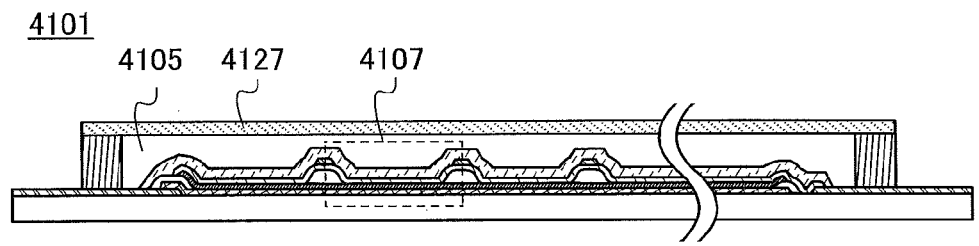

FIG. 13A is a plan view of a light-emitting device of one embodiment of the present invention, and FIG. 13B is a cross-sectional view taken along dashed-dotted line G-H in FIG. 13A. FIGS. 13C to 13E are cross-sectional views illustrating light-emitting devices of embodiments of the present invention.

A light-emitting device 4000 illustrated in FIGS. 13A and 13B includes a light-emitting element 4007 over a substrate 4005. In addition, the lighting device 4000 includes a substrate 4003 with unevenness on the outside of the substrate 4005. The light-emitting element 4007 includes a lower electrode 4013, an EL layer 4014, and an upper electrode 4015. The EL layer 4014 includes the organometallic complex containing at least any one of metals of iridium, platinum, palladium, and rhodium, and a ligand with a benzoquinazoline skeleton.

The lower electrode 4013 is electrically connected to an electrode 4009, and the upper electrode 4015 is electrically connected to an electrode 4011. In addition, an auxiliary wiring 4017 electrically connected to the lower electrode 4013 may be provided.

The substrate 4005 and a sealing substrate 4019 are bonded to each other by a sealant 4021. A desiccant 4023 is preferably provided between the sealing substrate 4019 and the light-emitting element 4007.

The substrate 4003 has the unevenness illustrated in FIG. 13A, whereby the extraction efficiency of light emitted from the light-emitting element 4007 can be increased. Instead of the substrate 4003, a diffusion plate 4027 may be provided on the outside of the substrate 4025 as in a light-emitting device 4001 illustrated in FIG. 13C.

FIGS. 13D and 13E illustrate top-emission light-emitting devices.

A light-emitting device 4100 illustrated in FIG. 13D includes a light-emitting element 4107 over a substrate 4125. The light-emitting element 4107 includes a lower electrode 4113, an EL layer 4114, and an upper electrode 4115.

The lower electrode 4113 is electrically connected to an electrode 4109, and the upper electrode 4115 is electrically connected to an electrode 4111. An auxiliary wiring 4117 electrically connected to the upper electrode 4115 may be provided. An insulating layer 4131 may be provided under the auxiliary wiring 4117.

The substrate 4125 and a sealing substrate 4103 with unevenness are bonded to each other by a sealant 4121. A planarization film 4105 and a barrier film 4129 may be provided between the sealing substrate 4103 and the light-emitting element 4107.

The sealing substrate 4103 has the unevenness illustrated in FIG. 13D, whereby the extraction efficiency of light emitted from the light-emitting element 4107 can be increased. Instead of the sealing substrate 4103, a diffusion plate 4127 may be provided over the light-emitting element 4107 as in a light-emitting device 4101 illustrated in FIG. 13E.

This embodiment can be combined with any of the other embodiments as appropriate.

Embodiment 4

In this embodiment, a touch sensor and a display module that can be combined with the light-emitting device of one embodiment of the present invention will be described with reference to FIGS. 14A and 14B, FIG. 15, FIG. 16, and FIG. 17.

Figure 14A:
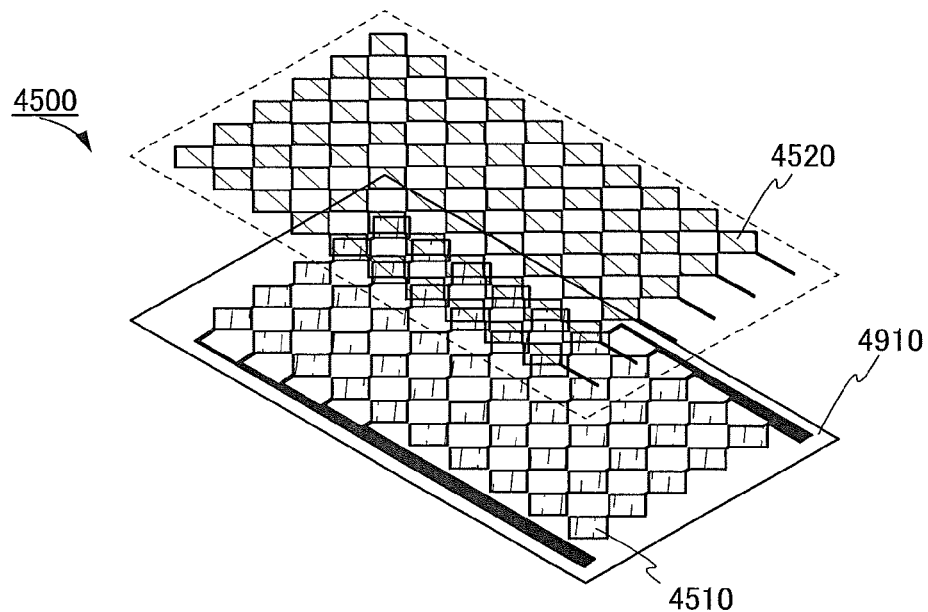
FIGS. 14A and 14B illustrate an example of a touch sensor.
Figure 14B:
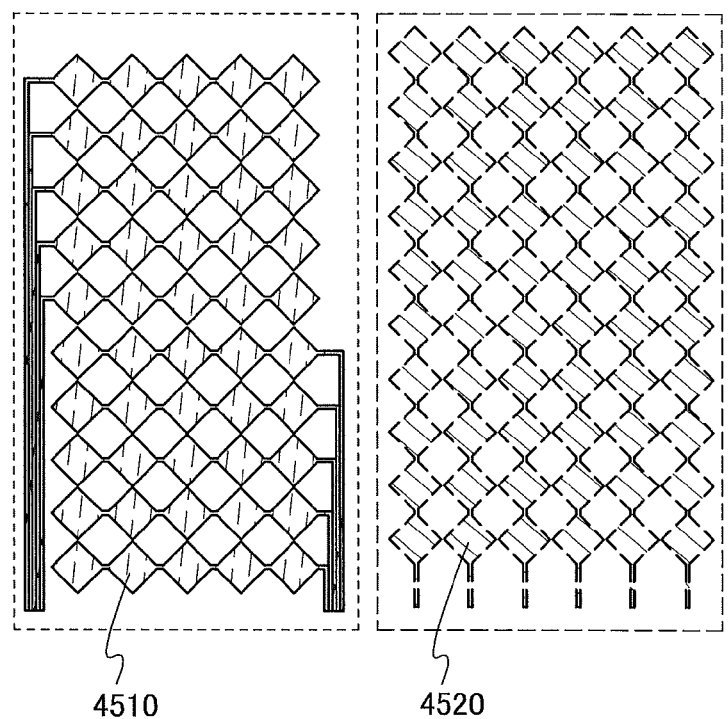

FIG. 14A is an exploded perspective view of a structural example of a touch sensor 4500. FIG. 14B is a plan view of a structural example of an electrode of the touch sensor 4500.

The touch sensor 4500 illustrated in FIGS. 14A and 14B includes, over a substrate 4910, a plurality of conductive layers 4510 arranged in the X-axis direction and a plurality of conductive layers 4520 arranged in the Y-axis direction intersecting with the X-axis direction. In FIGS. 14A and 14B, a plan view of the plurality of conductive layers 4510 of the touch sensor 4500 and a plan view of the plurality of conductive layers 4520 of the touch sensor 4500 are separately illustrated.

Figure 15:
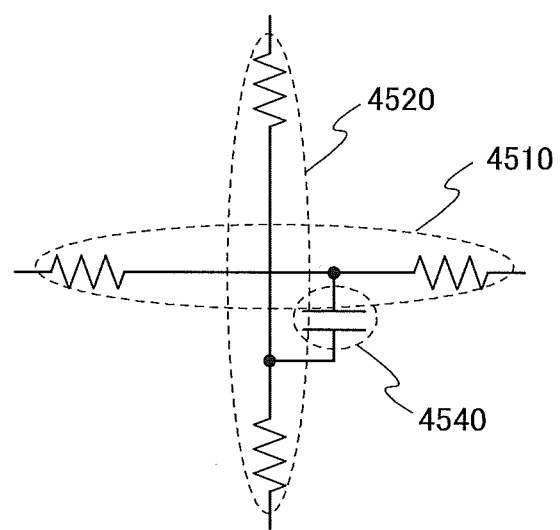
FIG. 15 is a circuit diagram of a touch sensor.

FIG. 15 is an equivalent circuit diagram of an intersection portion of the conductive layer 4510 and the conductive layer 4520 of the touch sensor 4500 illustrated in FIGS. 14A and 14B. As illustrated in FIG. 15, a capacitor 4540 is formed at the intersection portion of the conductive layer 4510 and the conductive layer 4520.

The plurality of conductive layers 4510 and the plurality of conductive layers 4520 have structures in each of which a plurality of quadrangular conductive films are connected to each other. The plurality of conductive layers 4510 and the plurality of conductive layers 4520 are provided so that the quadrangular conductive films of the plurality of conductive layers 4510 do not overlap with the quadrangular conductive films of the plurality of conductive layers 4520. At the intersection portion of the conductive layer 4510 and the conductive layer 4520, an insulating film is provided between the conductive layer 4510 and the conductive layer 4520 to prevent the conductive layers 4510 and 4520 from being in contact with each other.

Figure 16:
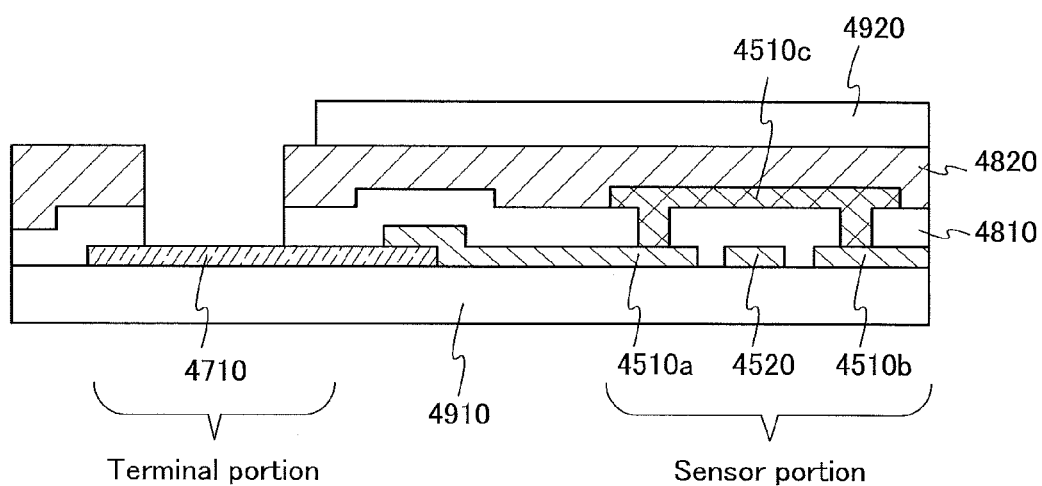
FIG. 16 illustrates an example of a touch sensor.

FIG. 16 is a cross-sectional view illustrating a portion where the conductive layers 4510 (conductive layers 4510a, 4510b, and 4510c) and the conductive layer 4520 of the touch sensor 4500 in FIGS. 14A and 14B intersect with each other.

As illustrated in FIG. 16, the conductive layers 4510 include the conductive layer 4510a and the conductive layer 4510b in the first layer and the conductive layer 4510c in the second layer over an insulating layer 4810. The conductive layer 4510a and the conductive layer 4510b are connected by the conductive layer 4510c. The conductive layer 4520 is formed using the conductive film in the first layer. An insulating layer 4820 is formed so as to cover the conductive layers 4510 and 4520 and an electrode 4710. As the insulating layers 4810 and 4820, silicon oxynitride films may be formed, for example. A base film formed using an insulating film may be provided between the substrate 4910, and the conductive layers 4510 and the electrode 4710. As the base film, for example, a silicon oxynitride film can be formed.

The conductive layers 4510 and the conductive layer 4520 are formed using a conductive material that transmits visible light, such as indium tin oxide containing silicon oxide, indium tin oxide, zinc oxide, indium zinc oxide, or zinc oxide to which gallium is added.

The conductive layer 4510a is connected to the electrode 4710. A terminal for connection to an FPC is formed using the electrode 4710. Like the conductive layers 4510, the conductive layer 4520 is connected to the electrode 4710. The electrode 4710 can be formed of a tungsten film, for example.

The insulating layer 4820 is formed so as to cover the conductive layers 4510 and 4520 and the electrode 4710. An opening portion is formed in the insulating layers 4810 and 4820 over the electrode 4710 to connect the electrode 4710 and the FPC electrically. A substrate 4920 is attached to the insulating layer 4820 using an adhesive, an adhesive film, or the like. The substrate 4910 side is bonded to a color filter substrate of a display panel with an adhesive or an adhesive film, so that a touch panel is completed.

Next, a display module that can be formed using the light-emitting device of one embodiment of the present invention is described with reference to FIG. 17.

Figure 17:
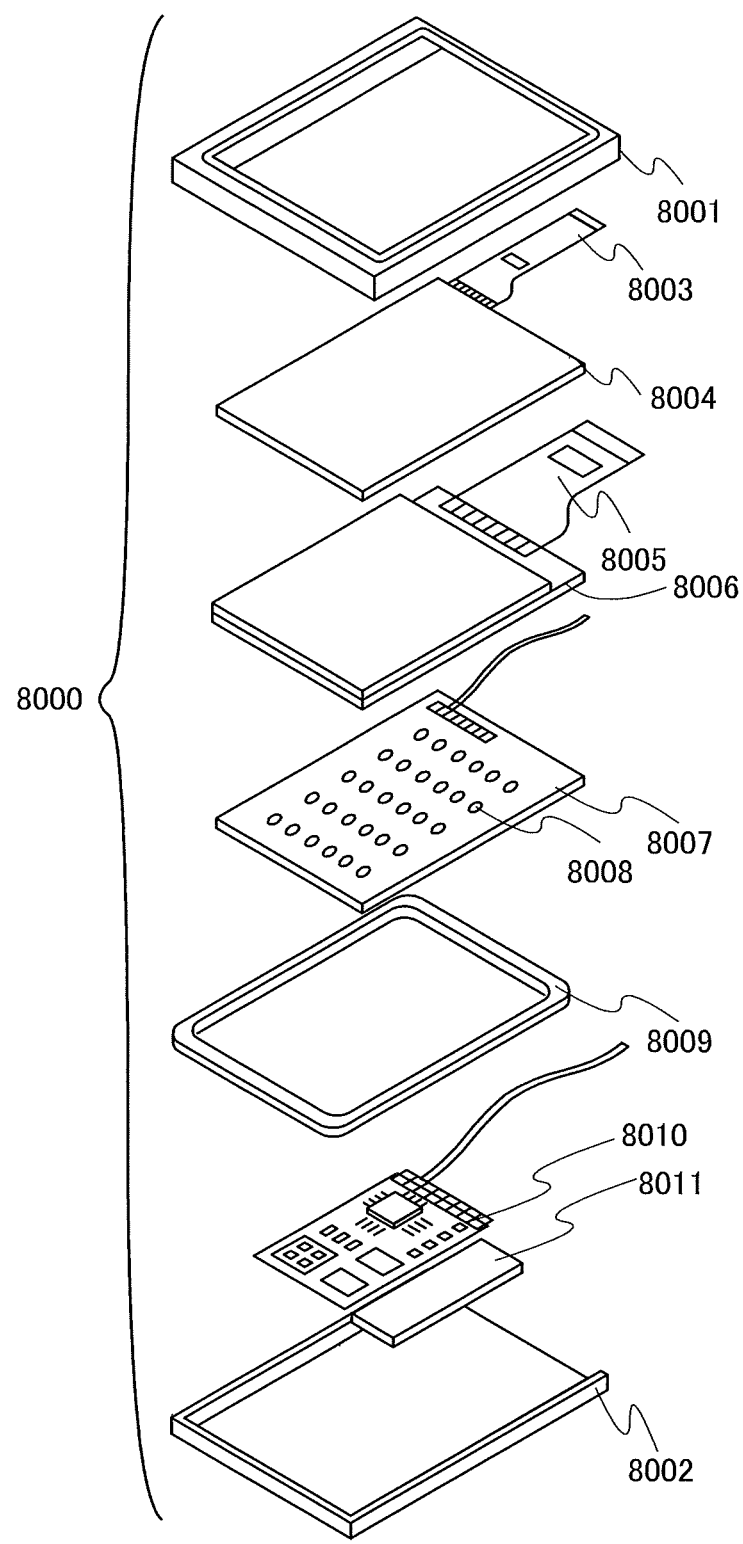
FIG. 17 illustrates an example of a display module.

In a display module 8000 in FIG. 17, a touch panel 8004 connected to an FPC 8003, a display panel 8006 connected to an FPC 8005, a backlight unit 8007, a frame 8009, a printed circuit board 8010, and a battery 8011 are provided between an upper cover 8001 and a lower cover 8002.

The shapes and sizes of the upper cover 8001 and the lower cover 8002 can be changed as appropriate in accordance with the sizes of the touch panel 8004 and the display panel 8006.

The touch panel 8004 can be a resistive touch panel or a capacitive touch panel and may be formed so as to overlap with the display panel 8006. A counter substrate (sealing substrate) of the display panel 8006 can have a touch panel function. A photosensor may be provided in each pixel of the display panel 8006 so that the touch panel 8004 can function as an optical touch panel.

The backlight unit 8007 includes a light source 8008. The light source 8008 may be provided at an end portion of the backlight unit 8007 and a light diffusing plate may be used.

The frame 8009 protects the display panel 8006 and functions as an electromagnetic shield for blocking electromagnetic waves generated by the operation of the printed circuit board 8010. The frame 8009 may function as a radiator plate.

The printed circuit board 8010 is provided with a power supply circuit and a signal processing circuit for outputting a video signal and a clock signal. As a power source for supplying power to the power supply circuit, an external commercial power source or a power source using the battery 8011 provided separately may be used. The battery 8011 can be omitted in the case of using a commercial power source.

The display module 8000 can be additionally provided with a member such as a polarizing plate, a retardation plate, or a prism sheet.

This embodiment can be combined with any of the other embodiments as appropriate.

Embodiment 5

In this embodiment, examples of electronic devices and lighting devices to which the light-emitting device of one embodiment of the present invention is applied will be described with reference to FIGS. 4A to 4E and FIGS. 5A and 5B.

Electronic devices of this embodiment each include the light-emitting device of one embodiment of the present invention in a display portion. Lighting devices of this embodiment each include the light-emitting device of one embodiment of the present invention in a light-emitting portion (a lighting portion). Low-power-consumption electronic devices and lighting devices can be provided by adopting the light-emitting device of one embodiment of the present invention.

Examples of electronic devices to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic devices and lighting devices are illustrated in FIGS. 4A to 4E and FIGS. 5A and 5B.

FIG. 4A illustrates an example of a television device. In a television device 7100, a display portion 7102 is incorporated in a housing 7101. The display portion 7102 is capable of displaying images. The light-emitting device of one embodiment of the present invention can be used for the display portion 7102. In addition, here, the housing 7101 is supported by a stand 7103.

The television device 7100 can be operated with an operation switch provided in the housing 7101 or a separate remote controller 7111. With operation keys of the remote controller 7111, channels and volume can be controlled and images displayed on the display portion 7102 can be controlled. The remote controller 7111 may be provided with a display portion for displaying data output from the remote controller 7111.

Note that the television device 7100 is provided with a receiver, a modem, and the like. With the use of the receiver, general television broadcasting can be received. Moreover, when the television device is connected to a communication network with or without wires via the modem, one-way (from a sender to a receiver) or two-way (between a sender and a receiver or between receivers) information communication can be performed.

FIG. 4B illustrates an example of a computer. A computer 7200 includes a main body 7201, a housing 7202, a display portion 7203, a keyboard 7204, an external connection port 7205, a pointing device 7206, and the like. Note that this computer is fabricated by using the light-emitting device of one embodiment of the present invention for the display portion 7203.

FIG. 4C illustrates an example of a portable game machine. A portable game machine 7300 has two housings, a housing 7301a and a housing 7301b, which are connected with a joint portion 7302 so that the portable game machine can be opened or closed. The housing 7301a incorporates a display portion 7303a, and the housing 7301b incorporates a display portion 7303b. In addition, the portable game machine illustrated in FIG. 4C includes a speaker portion 7304, a recording medium insertion portion 7305, an operation key 7306, a connection terminal 7307, a sensor 7308 (a sensor having a function of measuring or sensing force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), an LED lamp, a microphone, and the like. It is needless to say that the structure of the portable game machine is not limited to the above structure as long as the light-emitting device of one embodiment of the present invention is used for at least either the display portion 7303a or the display portion 7303b, or both, and may include other accessories as appropriate. The portable game machine illustrated in FIG. 4C has a function of reading out a program or data stored in a recoding medium to display it on the display portion, and a function of sharing information with another portable game machine by wireless communication. Note that functions of the portable game machine illustrated in FIG. 4C are not limited to them, and the portable game machine can have various functions.

FIG. 4D illustrates an example of a cellular phone. A cellular phone 7400 is provided with a display portion 7402 incorporated in a housing 7401, an operation button 7403, an external connection port 7404, a speaker 7405, a microphone 7406, and the like. Note that the cellular phone 7400 is fabricated by using the light-emitting device of one embodiment of the present invention for the display portion 7402.

When the display portion 7402 of the cellular phone 7400 illustrated in FIG. 4D is touched with a finger or the like, data can be input into the cellular phone. Further, operations such as making a call and creating e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, an input mode mainly for inputting characters is selected for the display portion 7402 so that characters displayed on the screen can be input.

When a sensing device including a sensor such as a gyroscope sensor or an acceleration sensor for sensing inclination is provided inside the cellular phone 7400, display on the screen of the display portion 7402 can be automatically changed in direction by determining the orientation of the cellular phone 7400 (whether the cellular phone 7400 is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by the display portion 7402 while in touch with the palm or the finger, whereby personal authentication can be performed. Further, when a backlight or a sensing light source which emits near-infrared light is provided in the display portion, an image of a finger vein, a palm vein, or the like can be taken.

FIG. 4E illustrates an example of a foldable tablet terminal (in an open state). A tablet terminal 7500 includes a housing 7501a, a housing 7501b, a display portion 7502a, and a display portion 7502b. The housing 7501a and the housing 7501b are connected by a hinge 7503 and can be opened and closed using the hinge 7503 as an axis. The housing 7501a includes a power switch 7504, operation keys 7505, a speaker 7506, and the like. Note that the tablet terminal 7500 is fabricated by using the light-emitting device of one embodiment of the present invention for either the display portion 7502a or the display portion 7502b, or both.

Part of the display portion 7502a or the display portion 7502b can be used as a touch panel region, where data can be input by touching displayed operation keys. For example, a keyboard can be displayed on the entire region of the display portion 7502a so that the display portion 7502a is used as a touch panel, and the display portion 7502b can be used as a display screen.

Figure 5A:
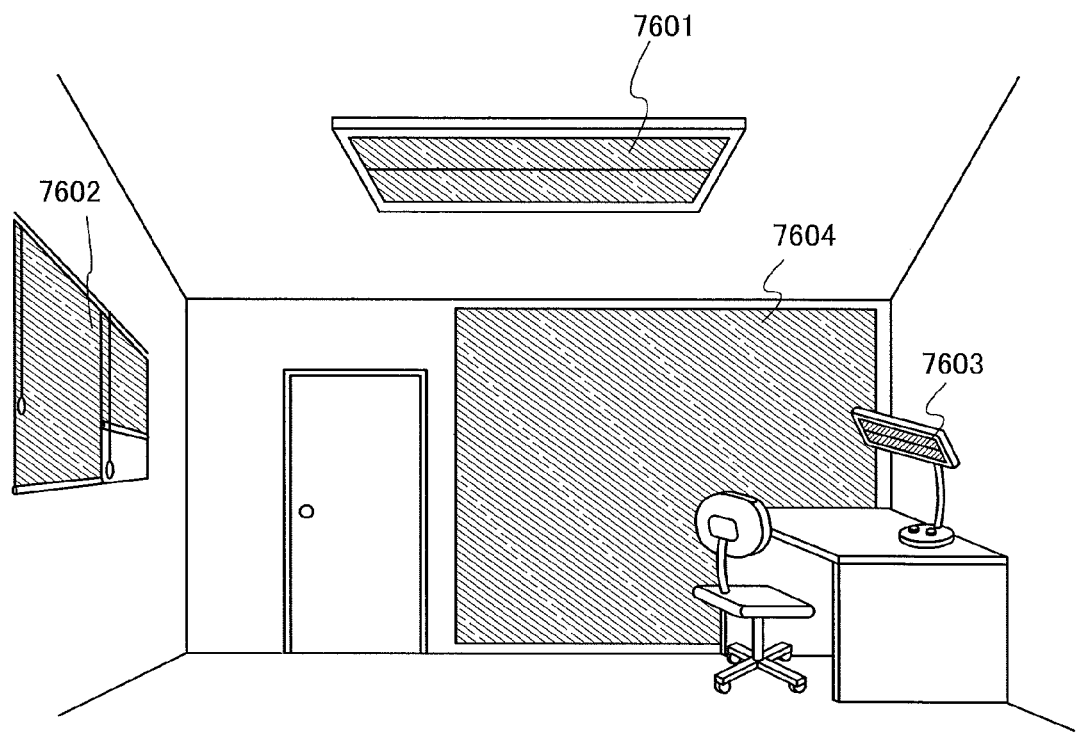
FIGS. 5A and 5B illustrate examples of a lighting device.

An indoor lighting device 7601, a roll-type lighting device 7602, a desk lamp 7603, and a planar lighting device 7604 illustrated in FIG. 5A are each an example of a lighting device which includes the light-emitting device of one embodiment of the present invention. Since the light-emitting device of one embodiment of the present invention can have a larger area, it can be used as a large-area lighting device. Further, since the light-emitting device is thin, the light-emitting device can be mounted on a wall.

Figure 5B:
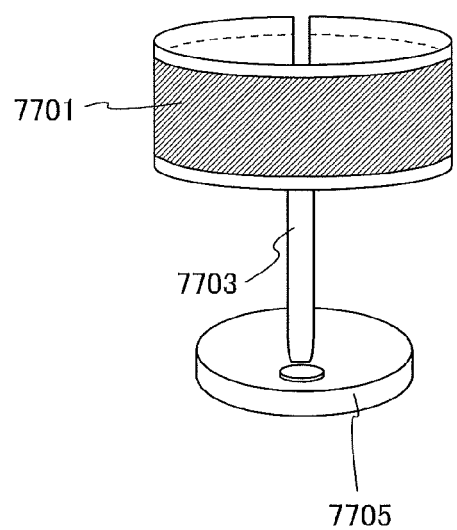

A desk lamp illustrated in FIG. 5B includes a lighting portion 7701, a support 7703, a support base 7705, and the like. The light-emitting device of one embodiment of the present invention is used for the lighting portion 7701. In one embodiment of the present invention, a lighting device whose light-emitting portion has a curved surface or a lighting device including a flexible lighting portion can be achieved. Such use of a flexible light-emitting device for a lighting device enables a place having a curved surface, such as the ceiling or dashboard of a motor vehicle, to be provided with the lighting device, as well as increases the degree of freedom in design of the lighting device.

This embodiment can be combined with any of the other embodiments as appropriate.

Example 1

Synthesis Example 1

A method for synthesizing bis[4-(2,5-dimethylphenyl)benzo[h]quinazolin-10-yl-κC,κN](2,2',6,6'-tetramethyl-3,5-heptanedionato-κ²O,O')iridium(III) (abbreviation: [Ir(dmpbqn)₂(dpm)]) represented by Structural Formula (101) will be described.

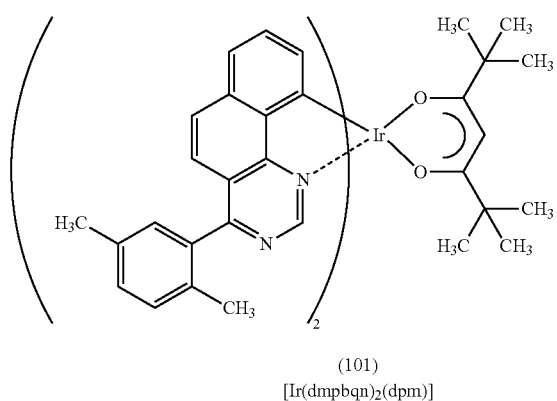

(101)
[Ir(dmpbqn)₂(dpm)]

Step 1: Synthesis of 5,6-Dihydrobenzo[h]quinazoline

In a 500-mL three-neck flask were put 16.8 g (115 mmol) of α-tetralone, 31.8 g (250 mmol) of N,N',N''-methylidynetrisformamide, and 35 mL of formamide. To this mixture, 1.2 g (6.2 mmol) of p-toluene sulfonic acid monohydrate was added and the mixture was stirred at 160° C. under a nitrogen stream for 9 hours. After stirring, this reactant was poured into a 2N aqueous solution of sodium hydroxide, and the mixture was stirred for 30 minutes. After stirring, hexane was added. An organic layer and an aqueous layer were separated and the organic layer was washed with water twice. After washing, anhydrous magnesium sulfate was added to the organic layer for drying. The resulting mixture was subjected to gravity filtration, and the filtrate was concentrated to give 8.5 g of a white solid in a yield of 40%. By nuclear magnetic resonance (NMR), the white solid was identified as 5,6-dihydrobenzo[h]quinazoline. Synthesis Scheme (a-1) of Step 1 is shown below.

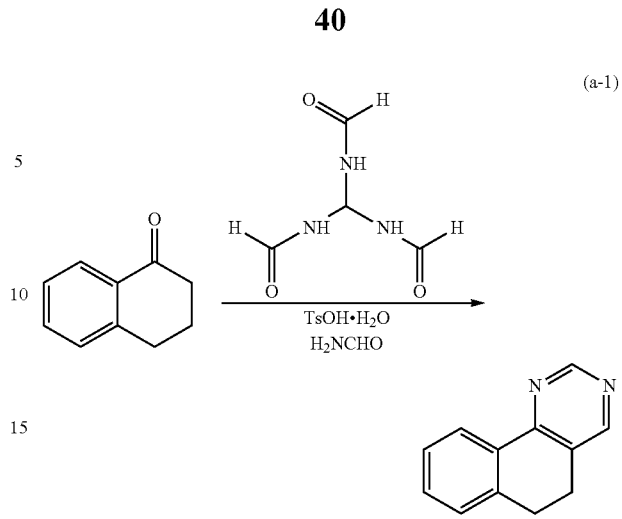

(a-1)

Step 2: Synthesis of Benzo[h]quinazoline

Into two batches (4.3 g each), 8.5 g (35.1 mmol) of 5,6-dihydrobenzo[h]quinazoline synthesized in Step 1 was divided, and reactions were each caused under the following condition. In a reaction container were put 4.3 g (23.3 mmol) of 5,6-dihydrobenzo[h]quinazoline and 1.5 g (46.6 mmol) of sulfur (crystals), and the mixture was stirred at 235° C. under a nitrogen stream for 2 hours. After the reactions, chloroform and water were added to the reacted solution of the two batches. An organic layer and an aqueous layer were separated and the organic layer was washed with a saturated aqueous solution of sodium hydrogen carbonate and a saturated aqueous solution of sodium chloride. After washing, anhydrous magnesium sulfate was added to the organic layer for drying. The resulting mixture was subjected to gravity filtration, and the filtrate was concentrated to give a yellow solid. The solid was purified by silica gel column chromatography. As the developing solvent, a 5:1 hexane-ethyl acetate mixed solvent was used. The resulting fraction was concentrated to give a yellow solid. Hexane was added to this solid and gravity filtration was performed. The resulting filtrate was concentrated to yield 6.1 g of a yellow solid in 73%. By NMR, the yellow solid was identified as benzo[h]quinazoline. Synthesis Scheme (a-2) of Step 2 is shown below.

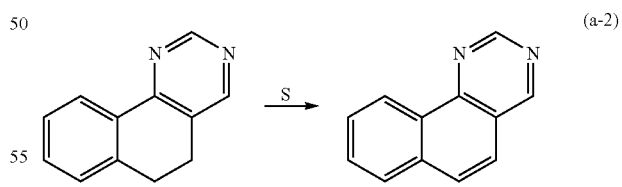

(a-2)

Step 3: Synthesis of Benzo[h]quinazolin-4(3H)-one

In a 300-ml recovery flask, 4.1 g (22.8 mmol) of benzo[h]quinazoline synthesized in Step 2 and 30 ml of glacial acetic acid were put and stirred. To this mixed solution, a mixed solution in which 50 g (91.2 mmol) of ammonium cerium(IV) nitrate was dissolved in 137 mL of water was added and stirring was performed at room temperature for 1 hour. After the predetermined time elapsed, a precipitate was suction-filtered to give a brown solid. To this solid, 300 mL of ethyl acetate was added. The mixture was heated using a hot plate and gravity-filtered to remove impurities. Anhydrous magnesium sulfate was added to the resulting filtrate for drying. The resulting mixture was subjected to gravity filtration, and the filtrate was concentrated to give a yellow solid. A saturated aqueous solution of sodium hydrogen carbonate was added to this yellow solid. The mixture was irradiated with ultrasonic waves and then suction-filtered to give 0.92 g of a yellow solid.

In addition, the acetic acid in the resulting filtrate obtained by the first suction filtration was distilled off. The resulting solution was subjected to extraction with ethyl acetate, and the solution of the extract was washed with a saturated aqueous solution of sodium hydrogen carbonate and a saturated aqueous solution of sodium chloride. After washing, anhydrous magnesium sulfate was added to an organic layer for drying. The resulting mixture was subjected to gravity filtration, and the filtrate was concentrated to give a yellow solid. Ethyl acetate was added to the solid. The mixture was irradiated with ultrasonic waves and then suction-filtered to give 1.3 g of a yellow solid. In total, 2.2 g of the yellow solid was obtained in a yield of 49%. By NMR, the yellow solid was identified as benzo[h]quinazolin-4(3H)-one. Synthesis Scheme (a-3) of Step 3 is shown below.

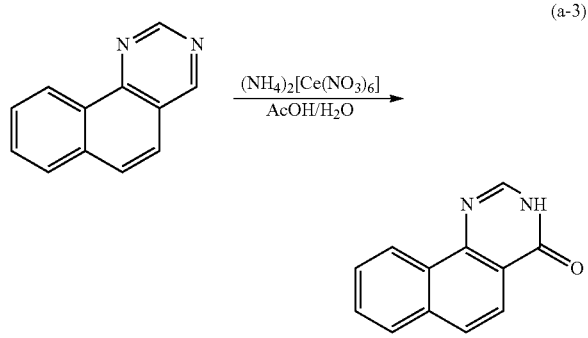

Step 4: Synthesis of 4-Chlorobenzo[h]quinazoline

In a 100-mL three-neck flask were put 2.2 g (11.2 mmol) of benzo[h]quinazolin-4(3H)-one synthesized in Step 3 and 20 mL of phosphoryl chloride, and the mixture was heated at 100° C. under a nitrogen stream for 5 hours. The phosphoryl chloride was distilled off from this mixture under a reduced pressure. The resulting residue was dissolved in ethyl acetate and this solution was added slowly to a saturated aqueous solution of sodium hydrogen carbonate. An aqueous layer and an organic layer of this mixture were separated and an organic substance was extracted from the aqueous layer using ethyl acetate. The resulting solution of the extract and the organic layer were combined and washed with a saturated aqueous solution of sodium hydrogen carbonate and a saturated aqueous solution of sodium chloride. After washing, anhydrous magnesium sulfate was added to the organic layer for drying, and the resulting mixture was subjected to gravity filtration to give a filtrate. The resulting filtrate was concentrated to give a solid. This solid was purified by silica gel column chromatography. As the developing solvent, a 2:1 hexane-ethyl acetate mixed solvent was used. The resulting fraction was concentrated to give 1.7 g of a yellow solid in a yield of 73%. By NMR, the yellow solid was identified as 4-chlorobenzo[h]quinazoline. Synthesis Scheme (a-4) of Step 4 is shown below.

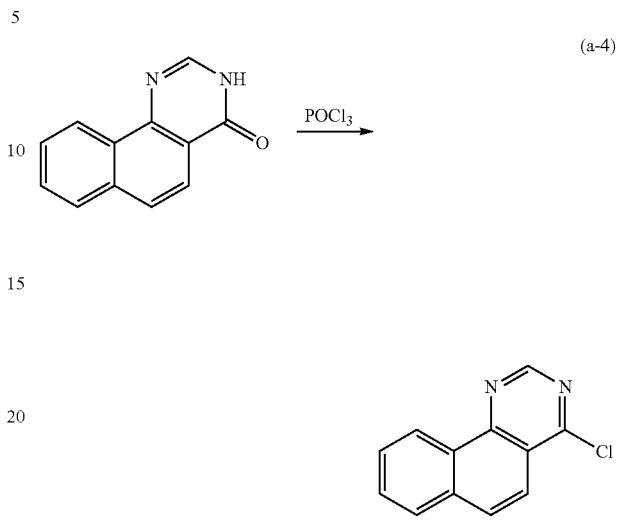

Step 5: Synthesis of 4-(2,5-Dimethylphenyl)benzo[h]quinazoline

In a 100-ml round-bottom flask were put 1.9 g (8.7 mmol) of 4-chlorobenzo[h]quinazoline synthesized in Step 4, 2.0 g (13 mmol) of 2,5-dimethylphenylboronic acid, 1.4 g (13 mmol) of sodium carbonate, 0.072 g (0.102 mmol) of bis(triphenylphosphine)palladium(II)dichloride, 20 mL of acetonitrile, and 20 mL of water, and the air in the flask was replaced with argon. This reaction container was subjected to irradiation with microwaves (2.45 GHz, 100 W) for 2 hours to cause a reaction. Note that the irradiation with microwaves was performed using a microwave synthesis system (Discover, manufactured by CEM Corporation). Water was added to the reacted mixture, and an aqueous layer was subjected to extraction with dichloromethane. The solution of the extract was washed with a saturated aqueous solution of sodium hydrogen carbonate and a saturated aqueous solution of sodium chloride, and anhydrous magnesium sulfate was added to an organic layer for drying. The resulting mixture was subjected to gravity filtration, and the filtrate was concentrated to give an oily substance. The oily substance was purified by silica gel column chromatography. As the developing solvent, a 10:1 hexane-ethyl acetate mixed solvent was used. The resulting fraction was concentrated to give 1.8 g of a yellow oily substance in a yield of 74%. By NMR, the yellow oily substance was identified as 4-(2,5-dimethylphenyl)benzo[h]quinazoline. Synthesis Scheme (a-5) of Step 5 is shown below.

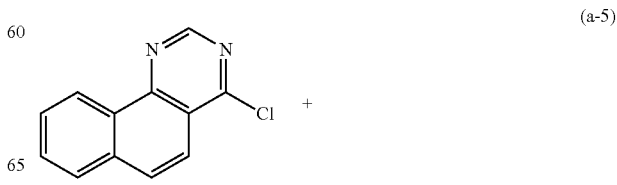

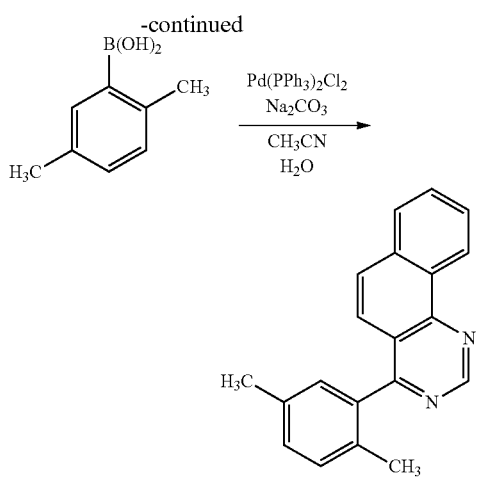

Step 6: Synthesis of Di-μ-chloro-tetrakis[4-(2,5-dimethylphenyl)benzo[h]quinazolin-10-yl-κC,κN]diiridium(III) (abbreviation: [Ir(dmpbqn)$_2$Cl]$_2$)

In a 100-mL round-bottom flask were put 1.8 g (6.4 mmol) of 4-(2,5-dimethylphenyl)benzo[h]quinazoline synthesized in Step 5, 0.896 g (3.0 mmol) of iridium chloride monohydrate, 20 mL of 2-ethoxyethanol, and 5 mL of water, and the air in the flask was replaced with argon. This reaction container was subjected to irradiation with microwaves (2.45 GHz, 100 W) for 1 hour to cause a reaction. After the reaction, the reacted solution was concentrated to give a solid. Ethanol was added to this solid, and the mixture was irradiated to ultrasonic waves and then suction-filtered to give 1.9 g of a brown solid in a yield of 81%. Synthesis Scheme (a-6) of Step 6 is shown below.

(a-6)

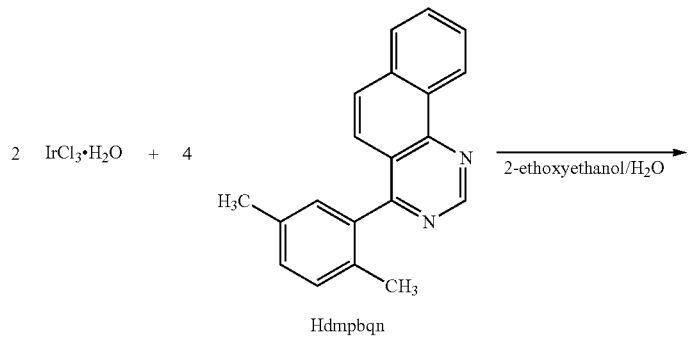

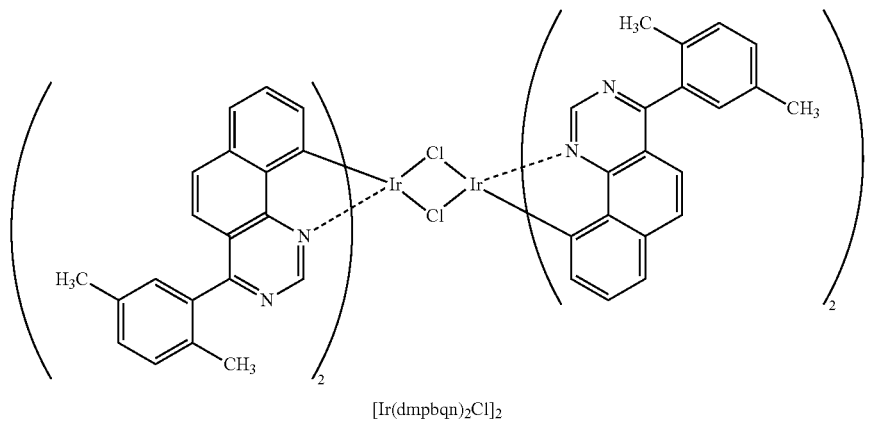

Step 7: Synthesis of [Ir(dmpbqn)₂(dpm)]

Figure 7:
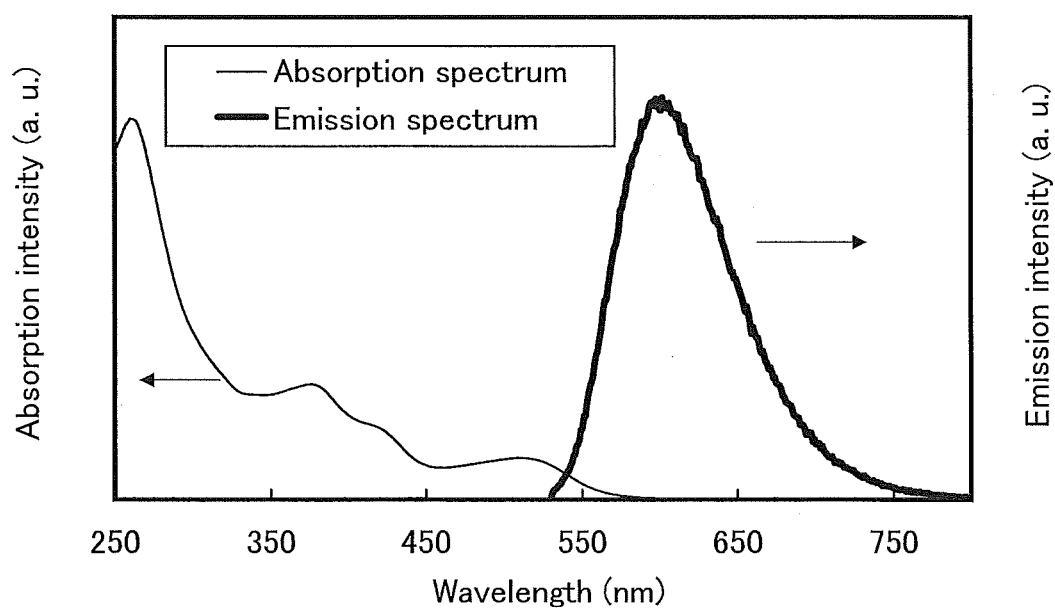
FIG. 7 shows an ultraviolet-visible absorption spectrum and an emission spectrum of the organometallic complex represented by Structural Formula (101).

In a 100-mL round-bottom flask were put 30 mL of 2-ethoxyethanol, 1.0 g (0.63 mmol) of [Ir(dmpbqn)₂Cl]₂, 0.35 g (1.9 mmol) of dipivaloylmethane, and 0.67 g (6.3 mmol) of sodium carbonate, and the air in the flask was replaced with argon. This reaction container was subjected to irradiation with microwaves (2.45 GHz, 120 W) for 2 hours to cause a reaction. After the reaction, water was added to the reacted mixture, and an aqueous layer was subjected to extraction with dichloromethane. The solution of the extract was washed with a saturated aqueous solution of sodium chloride, and anhydrous magnesium sulfate was added to an organic layer for drying. The resulting mixture was subjected to gravity filtration to give a filtrate. This filtrate was concentrated to give a red oily substance. The oily substance was purified by silica gel column chromatography. As the developing solvent, a 10:1 hexane-ethyl acetate mixed solvent was used. The resulting fraction was concentrated to give a red solid. Ethanol was added to this solid, so that the solid was dissolved in the ethanol. Then, water was added, so that a solid was precipitated. The solid was suction-filtered to give 0.73 g of a red solid in a yield of 61%. Synthesis Scheme (a-7) of Step 7 is shown below.

emission spectrum of a dichloromethane solution of [Ir(dmpbqn)₂(dpm)] were measured. The absorption spectrum was measured with the use of an ultraviolet-visible light spectrophotometer (V550, manufactured by Japan Spectroscopy Corporation) in the state where the dichloromethane solution (0.085 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.085 mmol/L) was put in a quartz cell at room temperature. FIG. 7 shows measurement results of the absorption spectrum and emission spectrum. In FIG. 7, the horizontal axis represents wavelength and the vertical axes represent absorption intensity and emission intensity. Note that the absorption spectrum in FIG. 7 is a result obtained by subtraction of the absorption spectrum of only dichloromethane that was put in a quartz cell from the measured absorption spectrum of the dichloromethane solution (0.085 mmol/L) in a quartz cell.

As shown in FIG. 7, [Ir(dmpbqn)₂(dpm)] has an emission peak at 602 nm, and orange light was observed from the dichloromethane solution.

Next, [Ir(dmpbqn)₂(dpm)] synthesized in this example was subjected to mass spectrometric (MS) analysis by liquid chromatography mass spectrometry (LC/MS).

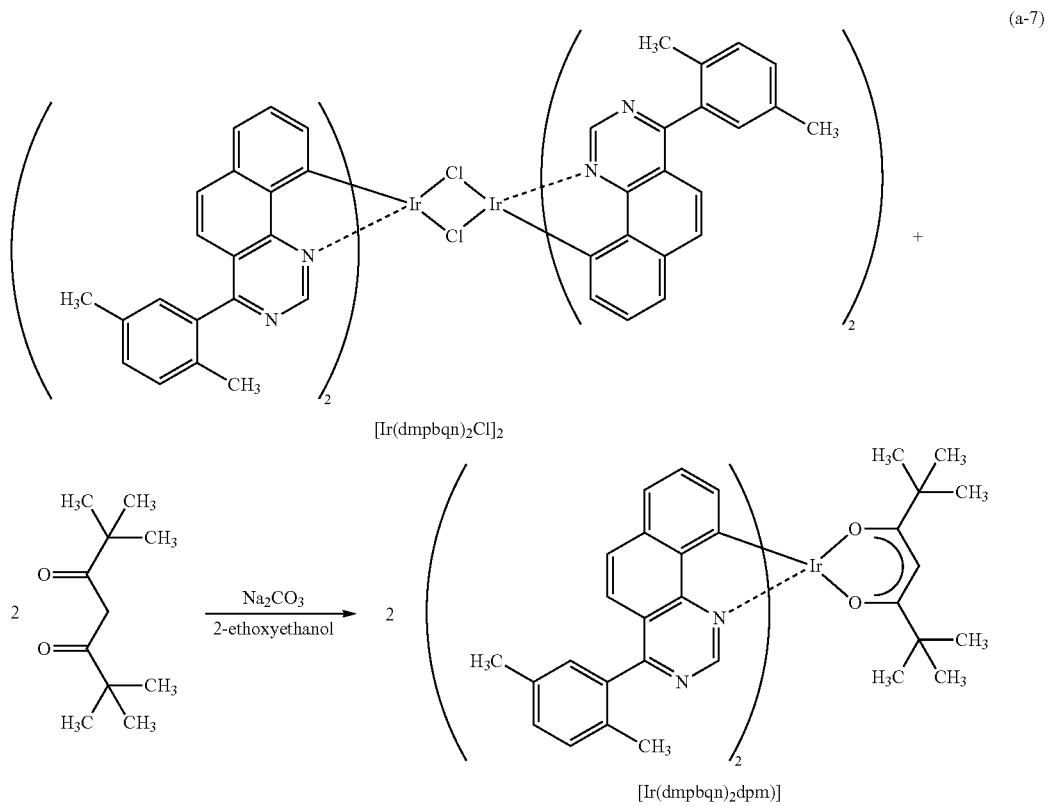

(a-7)

Figure 6:
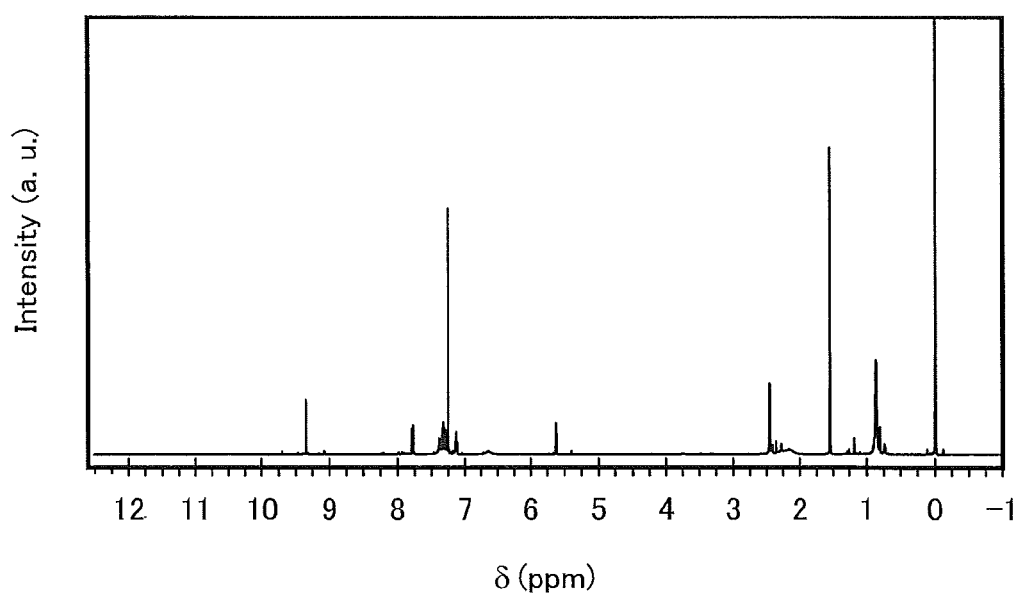
FIG. 6 is a $^1$H NMR chart of an organometallic complex represented by Structural Formula (101).

¹H NMR analysis results of the red solid obtained in Step 7 are described below. In addition, FIG. 6 shows a ¹H NMR chart. The results show that [Ir(dmpbqn)₂(dpm)] was obtained in this synthesis example.

¹H NMR. δ (CDCl₃): 0.86 (brs, 18H), 2.17 (brs, 6H), 2.46 (s, 6H), 5.62 (s, 1H), 6.64 (brs, 2H), 7.13 (t, 2H), 7.24-7.39 (m, 10H), 7.78 (d, 2H), 9.35 (s, 2H).

Next, an ultraviolet-visible absorption spectrum (hereinafter, simply referred to as absorption spectrum) and an The analysis by LC/MS was carried out with Acquity UPLC (manufactured by Waters Corporation), and Xevo G2 T of MS (manufactured by Waters Corporation).

In the MS analysis, ionization was carried out by an electrospray ionization (abbreviation: ESI) method. At this time, the capillary voltage and the sample cone voltage were set to 3.0 kV and 30 V, respectively, and detection was performed in a positive mode. A component which underwent the ionization under the above conditions and which exhibited a mass-to-charge ratio m/z of 943.36 was made to collide with an argon gas in a collision cell to dissociate into product ions. Energy (collision energy) for the collision with argon was 30 eV. A mass range for the measurement was m/z=100-1200. The detection results of the dissociated product ions by time-of-flight (TOF) MS are shown in FIG. 8.

Figure 8:
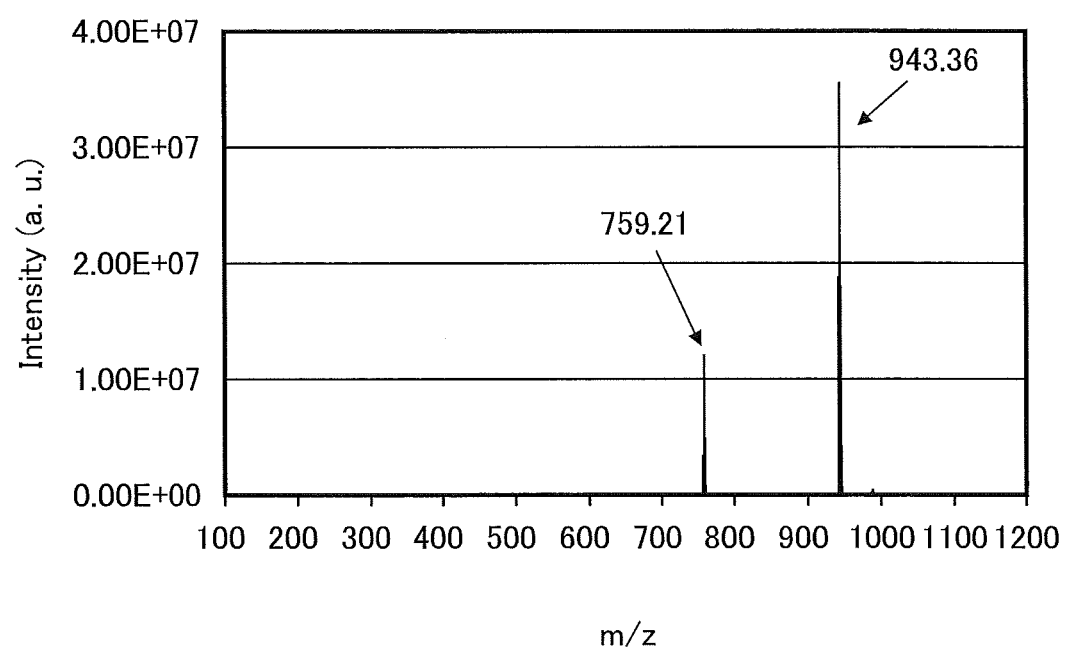
FIG. 8 shows results of LC/MS analysis of the organometallic complex represented by Structural Formula (101).

The results in FIG. 8 show that a product ion of [Ir(dmpbqn)$_2$(dpm)] was detected mainly around 759.21 (m/z). The results in FIG. 8 are characteristically derived from [Ir(dmpbqn)$_2$(dpm)] and can be thus regarded as important data in identification of [Ir(dmpbqn)$_2$(dpm)] contained in a mixture.

The product ion around 759.21 (m/z) is presumed to be a cation in the state where dipivaloylmethane is dissociated from [Ir(dmpbqn)$_2$(dpm)], which suggests that [Ir(dmpbqn)$_2$(dpm)] includes dipivaloylmethane Example 2

Figure 9:
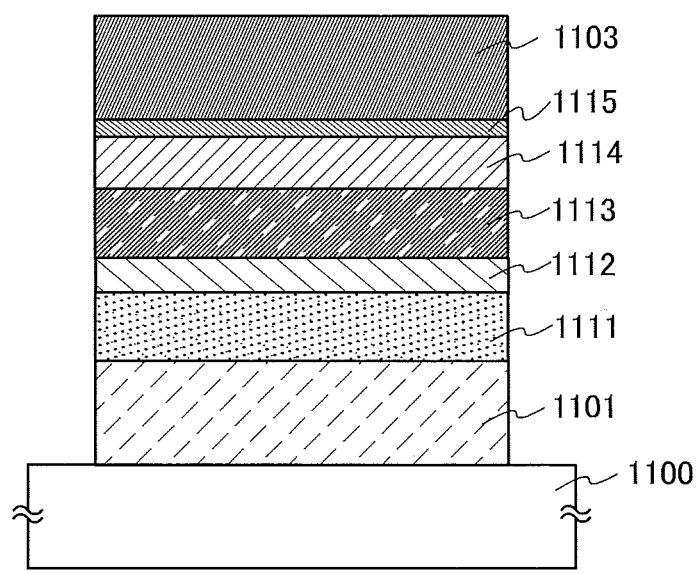
FIG. 9 illustrates a light-emitting element of Example 2.

In this example, a light-emitting element of one embodiment of the present invention will be described with reference to FIG. 9. Chemical formulae of materials used in this example are shown below.

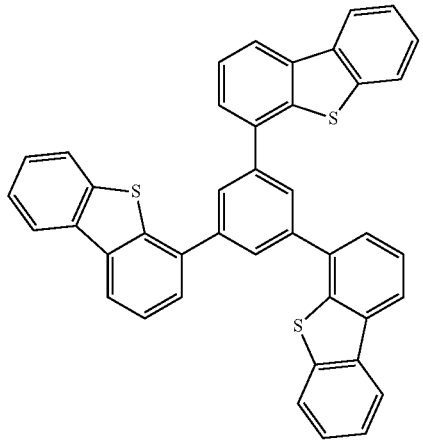

DBT3P-II

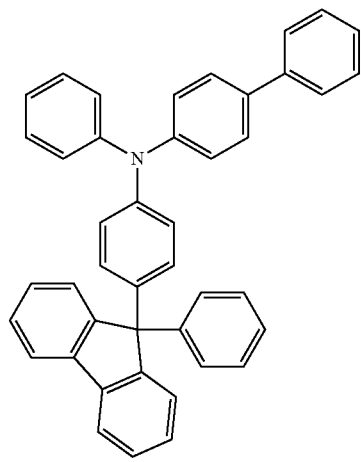

BPAFLP

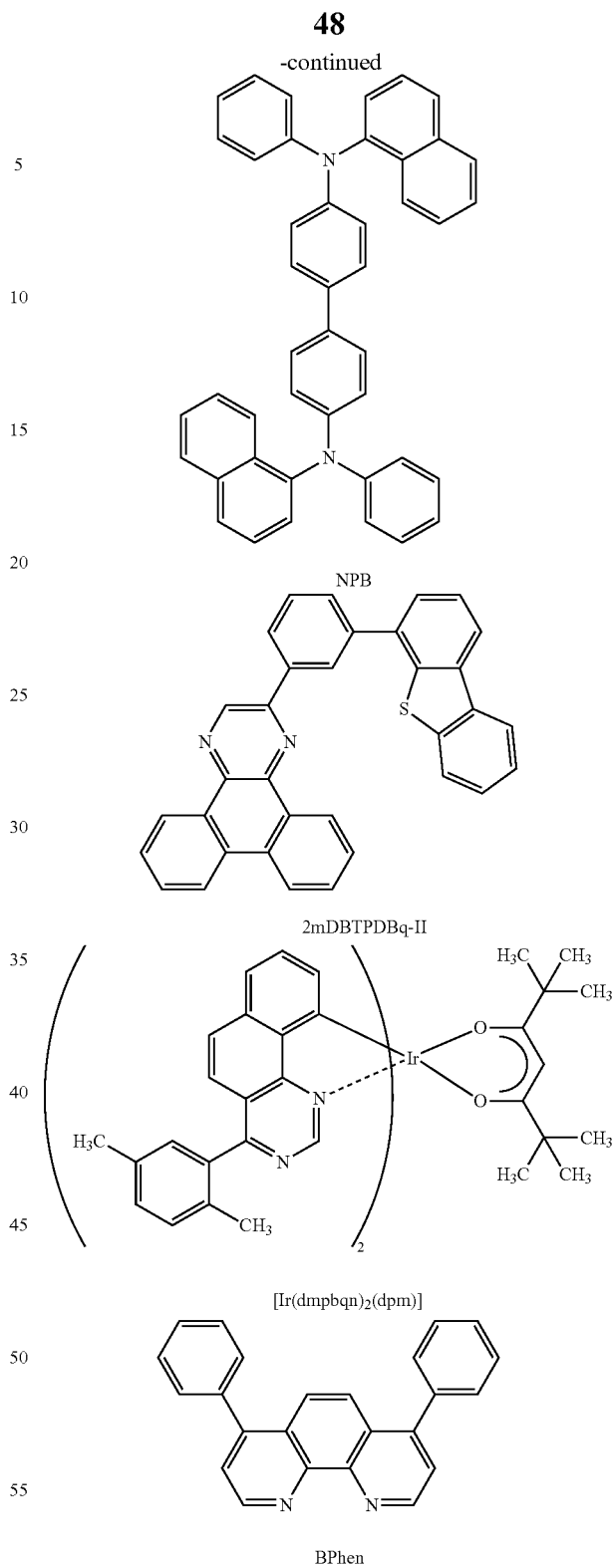

A method for fabricating a light-emitting element 1 of this example is described below.

(Light-Emitting Element 1)

First, indium tin oxide containing silicon oxide (ITSO) was deposited over a glass substrate 1100 by a sputtering method, whereby a first electrode 1101 was formed. The thickness thereof was 110 nm and the electrode area was 2 min×2 mm. Here, the first electrode 1101 is an electrode that functions as an anode of the light-emitting element.

Next, as pretreatment for forming the light-emitting element over the glass substrate 1100, UV-ozone treatment was performed for 370 seconds after washing of a surface of the substrate with water and baking that was performed at 200° C. for 1 hour.

After that, the glass substrate 1100 was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the glass substrate 1100 was cooled down for approximately 30 minutes.

Then, the glass substrate 1100 over which the first electrode 1101 was formed was fixed to a substrate holder provided in the vacuum evaporation apparatus so that the surface on which the first electrode 1101 was formed faced downward. The pressure in the vacuum evaporation apparatus was reduced to approximately $10^{-4}$ Pa. After that, over the first electrode 1101, 4,4',4''-(1,3,5-benzenetriyl)tri(dibenzothiophene) (abbreviation: DBT3P-II) and molybdenum(VI) oxide were deposited by co-evaporation by an evaporation method using resistance heating, so that a hole-injection layer 1111 was formed. The thickness of the hole-injection layer 1111 was set to 20 nm, and the weight ratio of DBT3P-II to molybdenum oxide was adjusted to 4:2 (=DBT3P-II: molybdenum oxide). Note that the co-evaporation method refers to an evaporation method in which evaporation is carried out from a plurality of evaporation sources at the same time in one treatment chamber.

Next, a film of 4-phenyl-4'-(9-phenylfluoren-9-yl)triphenylamine (abbreviation: BPAFLP) was formed to a thickness of 20 nm over the hole-injection layer 1111 to form a hole-transport layer 1112.

Further, a light-emitting layer 1113 was formed over the hole-transport layer 1112 by co-evaporation of 2-[3-(dibenzothiophen-4-yl)phenyl]dibenzo[f,h]quinoxaline (abbreviation: 2mDBTPDBq-II), 4,4'-bis[N-(1-naphthyl)-N-phenylamino]biphenyl (abbreviation: NPB), and bis[4-(2,5-dimethylphenyl)benzo[h]quinazolin-10-yl-κC,κN] (2,2',6,6'-tetramethyl-3,5-heptanedionato-κ$^2$O,O') iridium(III) (abbreviation: [Ir(dmpbqn)$_2$(dpm)]). Here, the weight ratio of 2mDBTPDBq-II to NPB and [Ir(dmpbqn)$_2$(dpm)] was adjusted to 0.8:0.2:0.01 (=2mDBTPDBq-II: NPB: [Ir(dmpbqn)$_2$(dpm)]). The thickness of the light-emitting layer 1113 was set to 40 nm.

Then, an electron-transport layer 1114 was formed over the light-emitting layer 1113 in such a way that a 20 nm thick film of 2mDBTPDBq-II was formed and a 20 nm thick film of bathophenanthroline (abbreviation: BPhen) was formed.

Further, over the electron-transport layer 1114, a film of lithium fluoride (LiF) was formed by evaporation to a thickness of 1 nm to form an electron-injection layer 1115.

Lastly, aluminum was deposited by evaporation to a thickness of 200 nm to form a second electrode 1103 functioning as a cathode. Thus, the light-emitting element 1 of this example was fabricated.

Note that in all the above evaporation steps, evaporation was performed by a resistance-heating method.

Table 1 shows an element structure of the light-emitting element fabricated as described above in this example.

TABLE 1

|  | First Electrode | Hole-injection Layer | Hole-transport Layer | Light-emitting Layer | Electron-transport Layer | Electron-injection Layer | Second Electrode |
|---|---|---|---|---|---|---|---|
| Light-emitting Element 1 | ITSO 110 nm | DBT3P-II: MoO$_x$ (=4:2) 20 nm | BPAFLP 20 nm | 2mDBTPDBq-II: NPB: [Ir(dmpbqn)$_2$(dpm)] (=0.8:0.2:0.01) 40 nm | 2mDBTPDBq-II 20 nm | BPhen 20 nm | LiF 1 nm | Al 200 nm |

In a glove box containing a nitrogen atmosphere, the light-emitting element 1 was sealed with a glass substrate so as not to be exposed to the air. Then, operation characteristics of the light-emitting element 1 were measured. Note that the measurement was carried out at room temperature (in an atmosphere kept at 25° C.).

Table 2 shows the voltage (V), current density (mA/cm$^2$), CIE chromaticity coordinates (x, y), current efficiency (cd/A), power efficiency (1 m/W), and external quantum efficiency (%) of the light-emitting element 1 at a luminance of 900 cd/m$^2$.

TABLE 2

|  | Voltage (V) | Current Density (mA/cm$^2$) | Chromaticity x | Chromaticity y | Current Efficiency (cd/A) | Power Efficiency (lm/W) | External Quantum Efficiency (%) |
|---|---|---|---|---|---|---|---|
| Light-emitting Element 1 | 3.0 | 1.6 | 0.54 | 0.45 | 58 | 61 | 21 |

Table 2 shows that the light-emitting element 1 has low drive voltage and high current efficiency and external quantum efficiency.

As shown in Table 2, the CIE chromaticity coordinates of the light-emitting element 1 were (x, y)=(0.54, 0.45) at a luminance of 900 cd/m$^2$. These results show that orange light emission originating from [Ir(dmpbqn)$_2$(dpm)] was provided from the light-emitting element 1.

Figure 10:
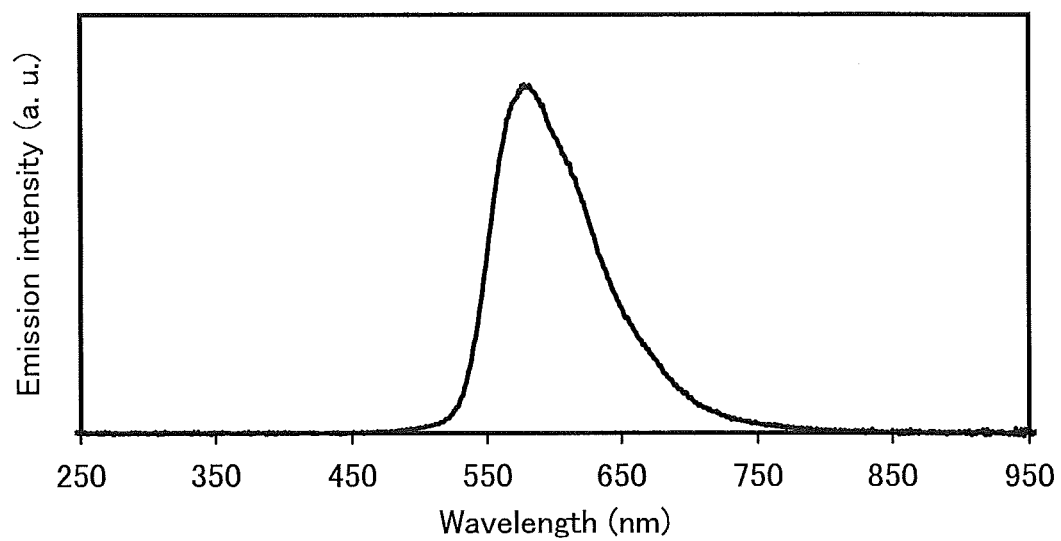
FIG. 10 is a graph showing an emission spectrum of a light-emitting element of Example 2.

FIG. 10 shows an emission spectrum when a current at a current density of 2.5 mA/cm$^2$ was supplied to the light-emitting element 1. As shown in FIG. 10, the emission spectrum of the light-emitting element 1 has a peak around 578 nm. This also suggests that light emission of the light-emitting element 1 originates from [Ir(dmpbqn)₂(dpm)] contained in the light-emitting layer 1113.

Example 3

Synthesis Example 2

A method for synthesizing bis[4-isobutylbenzo[h]quinazolin-10-yl-κC,κN](2,4-pentanedionato-κ²O,O')iridium (III) (abbreviation: [Ir(iBubqn)₂(acac)]) represented by Structural Formula (118) will be described.

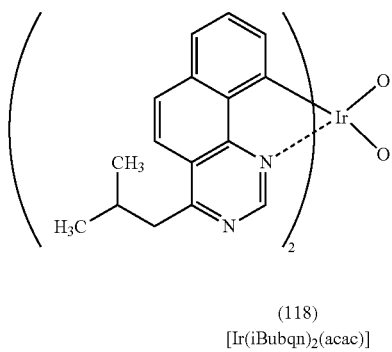

(118)
[Ir(iBubqn)₂(acac)]

Step 1: Synthesis of 4-Isobutylbenzo[h]quinazoline

In a 100-mL three-neck flask were put 0.53 g (2.5 mmol) of 4-chlorobenzo[h]quinazoline, 52 mg (0.148 mmol) of tris(2,4-pentanedionato)iron(III) (abbreviation: Fe(acac)₃), 25 mL of dehydrated tetrahydrofuran (THF), and 2.0 mL of 1-methyl-2-pyrrolidone (abbreviation: NMP), and the air in the flask was replaced with nitrogen. The flask was cooled with ice, 2.6 mL of isobutylmagnesium bromide solution (1 M in THF) (abbreviation: iBuMgBr) was added, and the mixture was stirred at room temperature for 16 hours. Then, 1 M hydrochloric acid was added, and an organic layer was subjected to extraction with ethyl acetate. The solution of the extract was washed with a saturated aqueous solution of sodium hydrogen carbonate and a saturated aqueous solution of sodium chloride, and dried over magnesium sulfate. After washing, anhydrous magnesium sulfate was added to the organic layer for drying. The resulting mixture was subjected to gravity filtration, and the filtrate was concentrated to give a residue. The residue was purified by silica gel column chromatography. As the developing solvent, first, dichloromethane was used; then, a 10:1 dichloromethane-ethyl acetate mixed solvent was used. The resulting fraction was concentrated to give 0.14 g of an orange oily substance in a yield of 24%. Synthesis Scheme (b-1) of Step 1 is shown below.

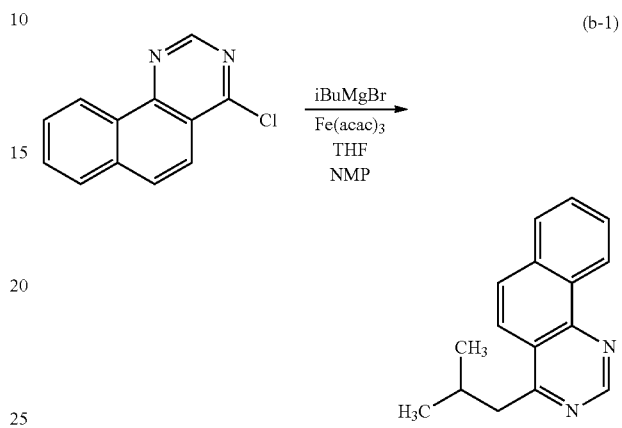

(b-1)

Step 2: Synthesis of Di-μ-chloro-tetrakis[4-isobutylbenzo[h]quinazolin-10-yl-κC,κN]diiridium(III) (abbreviation: [Ir(iBubqn)₂Cl]₂)

In a 100-mL round-bottom flask were put 0.14 g (0.59 mmol) of 4-isobutylbenzo[h]quinazoline, 0.088 g (0.30 mmol) of iridium chloride monohydrate, 15 mL of 2-ethoxyethanol, and 5 in L of water, and the air in the flask was replaced with argon. This reaction container was subjected to irradiation with microwaves (2.45 GHz, 100 W) for 1 hour to cause a reaction. After the reaction, the reacted solution was concentrated to give a solid. Dichloromethane and water were added to this solid to separate an organic layer and an aqueous layer, and the organic layer was washed with a saturated aqueous solution of sodium chloride. After washing, anhydrous magnesium sulfate was added to the organic layer for drying. The resulting mixture was subjected to gravity filtration, and the filtrate was concentrated to give 0.15 g of an orange solid in a yield of 72%. Synthesis Scheme (b-2) of Step 2 is shown below.

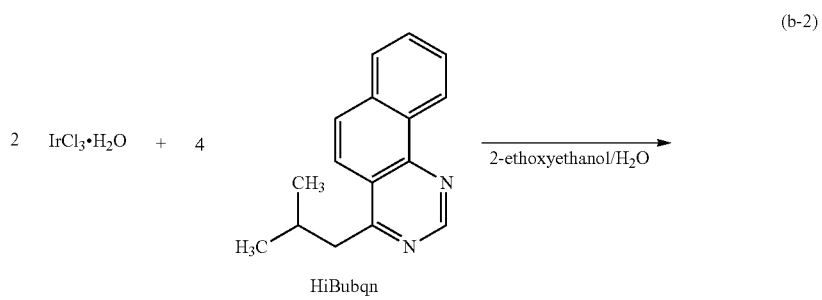

(b-2)

HiBubqn

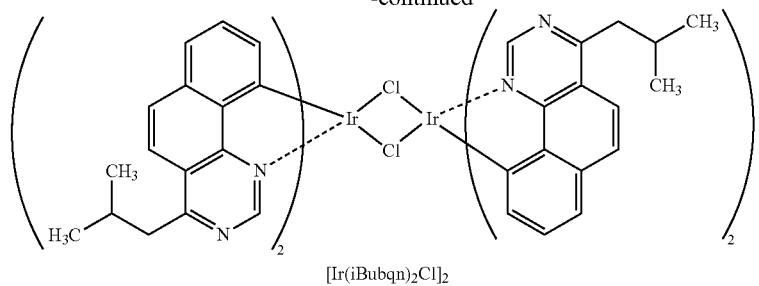

[Ir(iBubqn)₂Cl]₂

Step 3: Synthesis of [Ir(iBubqn)₂(acac)]

In a 100-mL round-bottom flask were put 30 mL of 2-ethoxyethanol, 0.15 g (0.11 mmol) of [Ir(iBubqn)₂Cl]₂, 0.074 g (0.74 mmol) of acetylacetone, and 0.16 g (1.5 mmol) of sodium carbonate, and the air in the flask was replaced with argon. This reaction container was subjected to irradiation with microwaves (2.45 GHz, 120 W) for 1 hour to cause a reaction. After the reaction, the reacted solution was concentrated to give a solid. Dichloromethane and water were added to this solid to separate an organic layer and an aqueous layer, and the organic layer was washed with a saturated aqueous solution of sodium chloride. After washing, anhydrous magnesium sulfate was added to the organic layer for drying. This filtrate was concentrated to give a solid. The solid was purified by silica gel column chromatography. As the developing solvent, a 20:1 dichloromethane-ethyl acetate mixed solvent was used. The resulting fraction was concentrated to yield 50 mg of a yellow solid in 30%. Synthesis Scheme (b-3) of Step 3 is shown below.

(b-3)

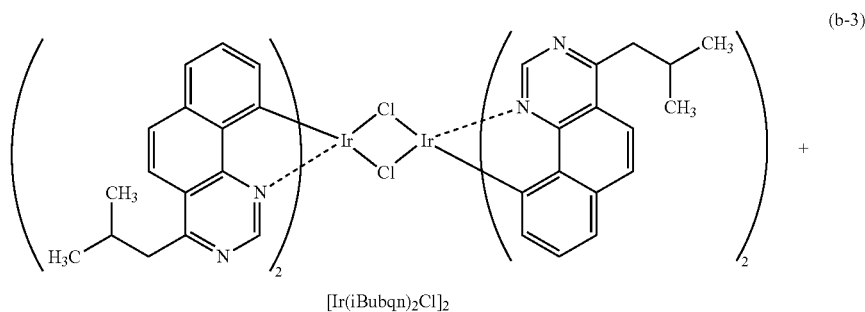

[Ir(iBubqn)₂Cl]₂  +

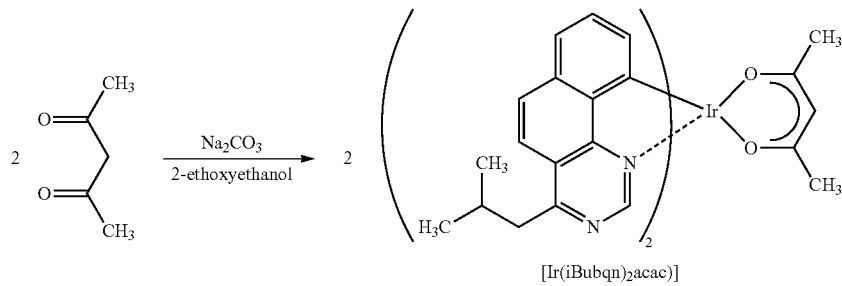

[Ir(iBubqn)₂acac)]

Figure 18:
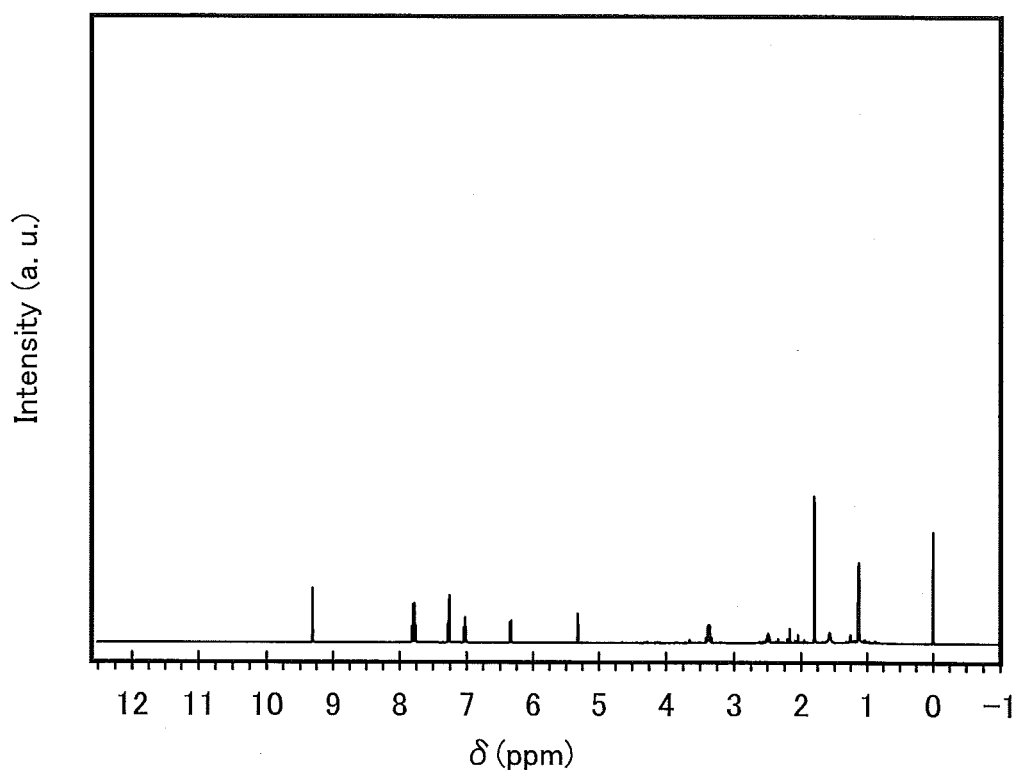
FIG. 18 is a $^1$H NMR chart of an organometallic complex represented by Structural Formula (118).

$^1$H NMR analysis results of the yellow solid obtained in Step 3 are described below. In addition, FIG. 18 shows a $^1$H NMR chart. The results show that [Ir(iBubqn)$_2$(acac)] was obtained in this synthesis example.

$^1$H NMR. δ (CDCl$_3$): 1.13 (d, 12H), 1.80 (s, 6H), 2.45-2.52 (m, 2H), 3.33-3.42 (m, 4H), 5.32 (s, 1H), 6.34 (d, 2H), 7.03 (t, 2H), 7.26-7.28 (m, 2H), 7.76-7.82 (m, 4H), 9.31 (s, 2H).

Figure 19:
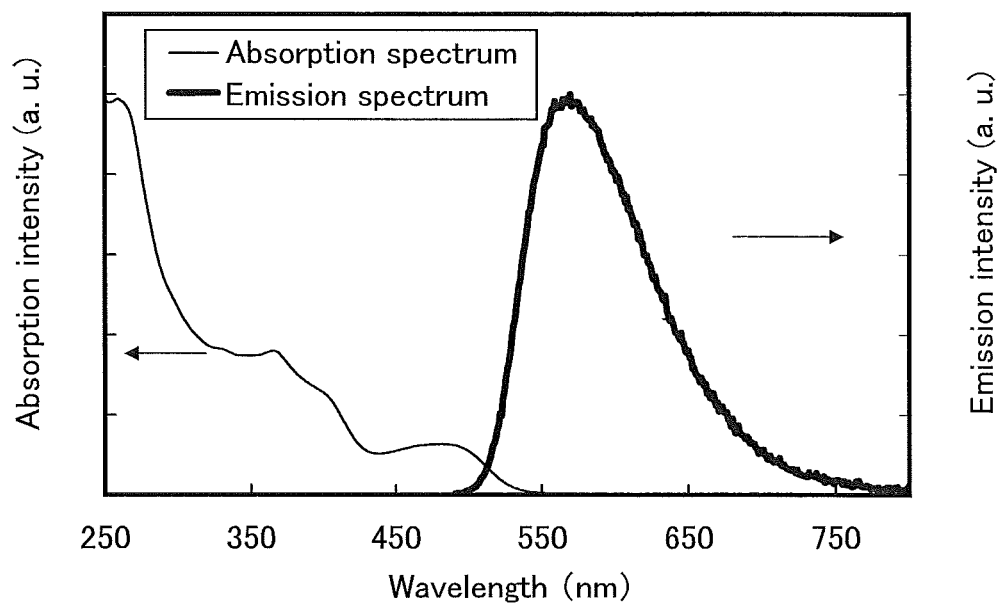
FIG. 19 shows an ultraviolet-visible absorption spectrum and an emission spectrum of the organometallic complex represented by Structural Formula (118).

Next, an ultraviolet-visible absorption spectrum (hereinafter, simply referred to as absorption spectrum) and an emission spectrum of a dichloromethane solution of [Ir(iBubqn)$_2$(acac)] were measured. The measurement method was similar to that used in Example 1. FIG. 19 shows measurement results of the absorption spectrum and emission spectrum. In FIG. 19, the horizontal axis represents wavelength and the vertical axes represent absorption intensity and emission intensity. Note that the absorption spectrum in FIG. 19 is a result obtained by subtraction of the absorption spectrum of only dichloromethane that was put in a quartz cell from the measured absorption spectrum of the dichloromethane solution (0.085 mmol/L) in a quartz cell.

As shown in FIG. 19, [Ir(iBubqn)$_2$(acac)] has an emission peak at 569 nm, and yellow light was observed from the dichloromethane solution.

Next, [Ir(iBubqn)$_2$(acac)] synthesized in this example was subjected to MS analysis by LC/MS.

A component which underwent the ionization under conditions similar to those used in Example 1 and which exhibited adz of 762.25 was made to collide with an argon gas in a collision cell to dissociate into product ions. Energy (collision energy) for the collision with argon was 30 eV. A mass range for the measurement was m/z=100-1200. The detection results of the dissociated product ions by time-of-flight (TOF) MS are shown in FIG. 20.

Figure 20:
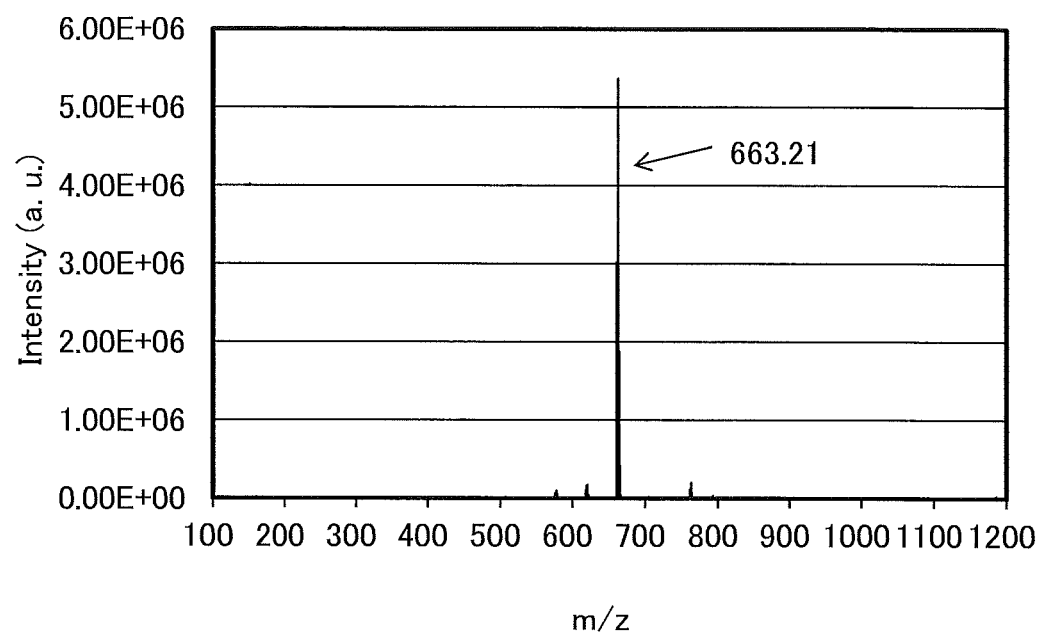
FIG. 20 shows results of LC/MS analysis of the organometallic complex represented by Structural Formula (118).

The results in FIG. 20 show that a product ion of [Ir(iBubqn)$_2$(acac)] was detected mainly around 663.21 (m/z). The results in FIG. 20 are characteristically derived from [Ir(iBubqn)$_2$(acac)] and can be thus regarded as important data in identification of [Ir(iBubqn)$_2$(acac)] contained in a mixture.

The product ion around 663.21 (m/z) is presumed to be a cation in the state where acetylacetone is dissociated from [Ir(iBubqn)$_2$(acac)], which suggests that [Ir(iBubqn)$_2$(acac)] includes acetylacetone.

This application is based on Japanese Patent Application serial no. 2013-031622 filed with Japan Patent Office on Feb. 21, 2013, the entire contents of which are hereby incorporated by reference.

What is claimed is:

1. A compound comprising a structure represented by a formula (G1):

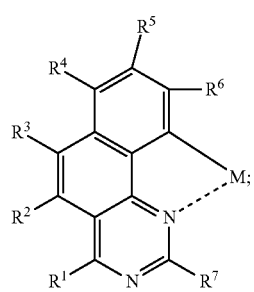

(G1)

$R^1$ represents a substituted or unsubstituted alkyl group having 1 to 6 carbon atoms, or a substituted or unsubstituted aryl group having 6 to 10 carbon atoms;

$R^2$ to $R^7$ separately represent hydrogen or a substituted or unsubstituted alkyl group having 1 to 6 carbon atoms; and M represents a metal.

2. The compound according to claim 1, wherein the metal is selected from iridium, platinum, palladium, and rhodium.

3. The compound according to claim 1, wherein the structure is represented by a formula (G2):

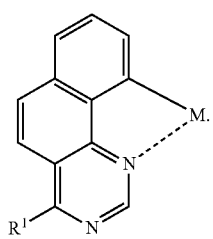

(G2)

4. A compound represented by a formula (G3):

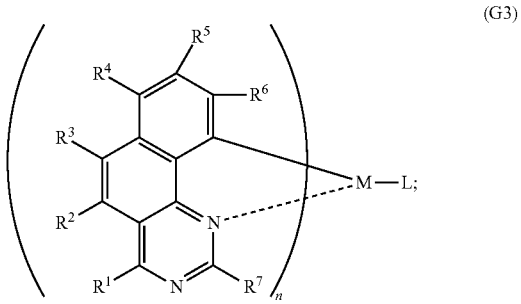

(G3)

$R^1$ represents a substituted or unsubstituted alkyl group having 1 to 6 carbon atoms, or a substituted or unsubstituted aryl group having 6 to 10 carbon atoms;

$R^2$ to $R^7$ separately represent hydrogen or a substituted or unsubstituted alkyl group having 1 to 6 carbon atoms;

M represents a metal; and

L represents a monoanionic ligand, wherein:
the metal is selected from iridium, platinum, palladium, and rhodium;
when M represents iridium or rhodium, n is 2; and
when M represents platinum or palladium, n is 1.

5. The compound according to claim 4, wherein the compound is represented by a formula (G4):

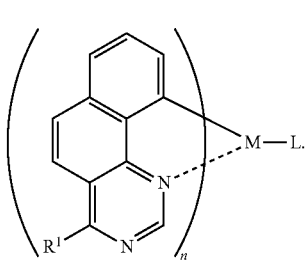

(G4)

6. The compound according to claim 4, wherein the monoanionic ligand is a monoanionic bidentate chelate ligand with a beta-diketone structure or a monoanionic bidentate chelate ligand in which two coordinating elements are both nitrogen.

7. The compound according to claim 6,
wherein:
the monoanionic ligand is represented by a formula (L1) or (L2):

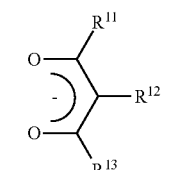

(L1)

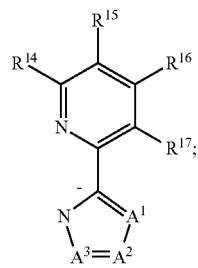

(L2)

$R^{11}$ to $R^{17}$ separately represent hydrogen or a substituted or unsubstituted alkyl group having 1 to 6 carbon atoms;
$A^1$ to $A^3$ separately represent nitrogen or carbon bonded to hydrogen or a substituent R; and
the substituent R represents an alkyl group having 1 to 6 carbon atoms or a phenyl group.

8. A compound represented by a formula (G5):

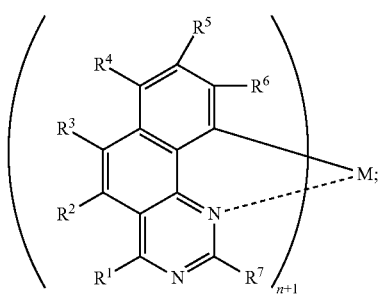

(G5)

$R^1$ represents a substituted or unsubstituted alkyl group having 1 to 6 carbon atoms, or a substituted or unsubstituted aryl group having 6 to 10 carbon atoms;
$R^2$ to $R^7$ separately represent hydrogen or a substituted or unsubstituted alkyl group having 1 to 6 carbon atoms; and
M represents a metal,
wherein:
the metal is selected from iridium, platinum, palladium, and rhodium;
when M represents iridium or rhodium, n is 2; and
when M represents platinum or palladium, n is 1.

9. The compound according to claim 8, wherein the compound is represented by a formula (G6):

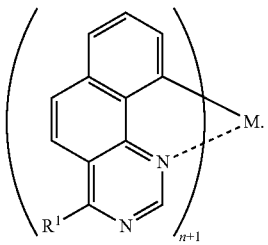

(G6)

10. A light-emitting device comprising:
a light emitting layer between a pair of electrodes, the light emitting layer comprising a compound comprising a structure represented by a formula (G1):

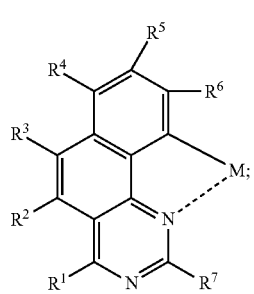

(G1)

$R^1$ represents a substituted or unsubstituted alkyl group having 1 to 6 carbon atoms, or a substituted or unsubstituted aryl group having 6 to 10 carbon atoms;
$R^2$ to $R^7$ separately represent hydrogen or a substituted or unsubstituted alkyl group having 1 to 6 carbon atoms; and
M represents a metal.

11. The light-emitting device according to claim 10, wherein the metal is selected from iridium, platinum, palladium, and rhodium.

12. The light-emitting device according to claim 10, wherein the structure is represented by a formula (G2):

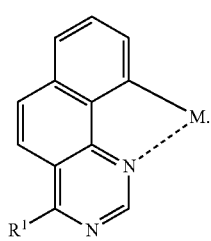

(G2)

13. A light-emitting device comprising:
a light emitting layer between a pair of electrodes, the light emitting layer comprising a compound represented by a formula (G3):

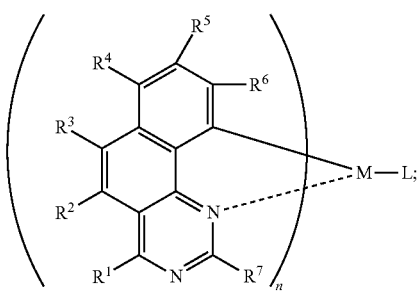

(G3)

R$^1$ represents a substituted or unsubstituted alkyl group having 1 to 6 carbon atoms, or a substituted or unsubstituted aryl group having 6 to 10 carbon atoms;

R$^2$ to R$^7$ separately represent hydrogen or a substituted or unsubstituted alkyl group having 1 to 6 carbon atoms;

M represents a metal; and

L represents a monoanionic ligand, wherein:

the metal is selected from iridium, platinum, palladium, and rhodium;

when M represents iridium or rhodium, n is 2; and when M represents platinum or palladium, n is 1.

14. The light-emitting device according to claim 13, wherein the compound is represented by a formula (G4):

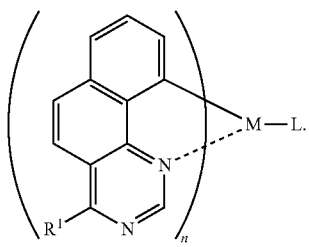

(G4)

15. The light-emitting device according to claim 13, wherein the monoanionic ligand is a monoanionic bidentate chelate ligand with a beta-diketone structure or a monoanionic bidentate chelate ligand in which two coordinating elements are both nitrogen.

16. The light-emitting device according to claim 15, wherein:

the monoanionic ligand is represented by a formula (L1) or (L2):

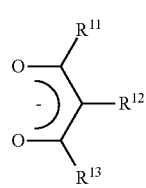

(L1)

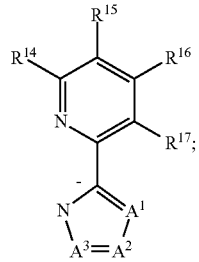

(L2)

R$^{11}$ to R$^{17}$ separately represent hydrogen or a substituted or unsubstituted alkyl group having 1 to 6 carbon atoms;

A$^1$ to A$^3$ separately represent nitrogen or carbon bonded to hydrogen or a substituent R; and the substituent R represents an alkyl group having 1 to 6 carbon atoms or a phenyl group.

17. A light-emitting device comprising:

a light emitting layer between a pair of electrodes, the light emitting layer comprising a compound represented by a formula (G5):

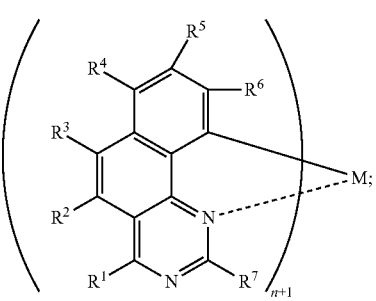

(G5)

R$^1$ represents a substituted or unsubstituted alkyl group having 1 to 6 carbon atoms, or a substituted or unsubstituted aryl group having 6 to 10 carbon atoms;

R$^2$ to R$^7$ separately represent hydrogen or a substituted or unsubstituted alkyl group having 1 to 6 carbon atoms; and M represents a metal, wherein:

the metal is selected from iridium, platinum, palladium, and rhodium;

when M represents iridium or rhodium, n is 2; and when M represents platinum or palladium, n is 1.

18. The light-emitting device according to claim 17, wherein the compound is represented by a formula (G6):

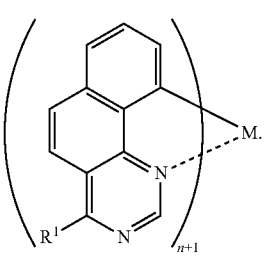

(G6)

19. An electronic appliance comprising the light-emitting device according to claim 10.

20. A lighting device comprising the light-emitting device according to claim 10.

* * * * *

UNITED STATES PATENT AND TRADEMARK OFFICE
CERTIFICATE OF CORRECTION

PATENT NO. : 9,444,059 B2
APPLICATION NO. : 14/184130
DATED : September 13, 2016
INVENTOR(S) : Inoue et al.

It is certified that error appears in the above-identified patent and that said Letters Patent is hereby corrected as shown below:

In the Specification

Column 6, Line 38; Change "rhodium, le represents" to --rhodium, $R^1$ represents--.

Column 23, Line 22; Change "triphenyl-N,N"-tris" to --triphenyl-N,N',N"-tris--.

Column 23, Line 44; Change ")-N-phenylamino]phenyl}" to --)-N'-phenylamino]phenyl}--.

Column 24, Line 51; Change "BP4 mPy)." to --BP4mPy).--.

Column 25, Line 21; Change "focused" to --formed--.

Column 26, Line 54; Change "tetralluoroquinodimethane" to --tetrafluoroquinodimethane--.

Column 31, Line 38; Change "fit" to --frit--.

Column 46, Line 61; Change "T of MS" to --Tof MS--.

Column 47, Line 18; Change "dipivaloylmethane" to --dipivaloylmethane.--.

Column 49, Line 1; Change "min×2 mm." to --mm×2 mm.--.

Column 50, Line 40; Change "(1 m/W)," to --(lm/W),--.

Column 52, Line 35; Change "and 5 in L of" to --and 5 mL of--.

Column 55, Line 29; Change "exhibited adz of" to --exhibited m/z of--.

Signed and Sealed this
Third Day of January, 2017

Michelle K. Lee
*Director of the United States Patent and Trademark Office*